(12) United States Patent
Li et al.

(10) Patent No.: US 9,833,415 B2
(45) Date of Patent: *Dec. 5, 2017

(54) 3D TUMOR TARGETING WITH DIAMAGNETIC REPULSION

(76) Inventors: Huanchen Li, Westford, MA (US); Wendy Wang, Westford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/866,740

(22) PCT Filed: Feb. 8, 2009

(86) PCT No.: PCT/US2009/033502
§ 371 (c)(1),
(2), (4) Date: Aug. 9, 2010

(87) PCT Pub. No.: WO2009/108478
PCT Pub. Date: Sep. 3, 2009

(65) Prior Publication Data
US 2011/0017222 A1   Jan. 27, 2011

Related U.S. Application Data

(60) Provisional application No. 61/032,420, filed on Feb. 28, 2008, provisional application No. 61/045,321, filed on Apr. 16, 2008, provisional application No. 61/078,434, filed on Jul. 6, 2008, provisional application No. 61/082,448, filed on Jul. 21, 2008, (Continued)

(51) Int. Cl.
| | |
|---|---|
| *A61K 9/50* | (2006.01) |
| *A61N 2/06* | (2006.01) |
| *A61N 2/00* | (2006.01) |
| *B82Y 15/00* | (2011.01) |
| *B82Y 25/00* | (2011.01) |

(52) U.S. Cl.
CPC .............. *A61K 9/5094* (2013.01); *A61N 2/06* (2013.01); *B82Y 15/00* (2013.01); *B82Y 25/00* (2013.01); *A61N 2/002* (2013.01)

(58) Field of Classification Search
CPC ........ A61K 9/5094; A61N 2/06; A61N 2/002; B82Y 15/00; B82Y 25/00
USPC ......... 600/12; 436/526; 435/173.1; 424/489, 424/490; 252/62.51 R, 62.53; 210/695, 210/222
See application file for complete search history.

(56) References Cited

U.S. PATENT DOCUMENTS 4,303,636 A * 12/1981 Gordon ..................... 424/491
4,874,346 A    10/1989 Wachspress et al.
(Continued)

FOREIGN PATENT DOCUMENTS

WO   PCT/US09/033502   3/2009

OTHER PUBLICATIONS

Gordon Paul Francis, ir-Dye pattern, 1986, http://www.wikipatents.com/GB-Patent-2173914/ir-dye-pattern.
(Continued)

*Primary Examiner* — David A Reifsnyder

(57) ABSTRACT

With externally applied magnetic fields, we will push and concentrate in vivo diamagnetic Bismuth particles or unipolar magnetic particles as a confined locus, cause the locus to move to a tumor, shape it to the tumor, then use near IR to heat the particles so to destroy the tumor by thermal ablation or hyperthermia treatment. We will then cause the locus to move to other tumors, and repeat the process, so to destroy all tumors and cure the cancer.

15 Claims, 5 Drawing Sheets

Related U.S. Application Data provisional application No. 61/097,579, filed on Sep. 17, 2008, provisional application No. 61/100,865, filed on Sep. 29, 2008, provisional application No. 61/106,153, filed on Oct. 16, 2008, provisional application No. 61/115,651, filed on Nov. 18, 2008, provisional application No. 61/120,541, filed on Dec. 8, 2008.

(56) References Cited

U.S. PATENT DOCUMENTS

| | | |
|---|---|---|
| 5,506,558 A | 4/1996 | Laube et al. |
| 6,372,840 B1 | 4/2002 | Shalati et al. |
| 6,392,518 B1 | 5/2002 | Abele et al. |
| 6,861,934 B2 | 3/2005 | Strom et al. |
| 7,073,513 B2 | 7/2006 | Cha et al. |
| 7,081,489 B2 | 7/2006 | Chen et al. |
| 2002/0079476 A1 | 6/2002 | Yadav et al. |
| 2002/0098359 A1 | 7/2002 | Kuehnle et al. |
| 2002/0155599 A1 | 10/2002 | Vellinger et al. |
| 2002/0172987 A1 | 11/2002 | Terstappen et al. |
| 2005/0249667 A1 | 11/2005 | Tuszynski et al. |
| 2006/0105170 A1 | 5/2006 | Dobson et al. |
| 2007/0092549 A1 | 4/2007 | Tuszynski et al. |
| 2007/0196281 A1 | 8/2007 | Jin et al. |
| 2008/0038806 A1* | 2/2008 | Fuhr .................. 435/173.1 |
| 2008/0053912 A1 | 3/2008 | Li |
| 2008/0279946 A1 | 11/2008 | Hainfeld |

OTHER PUBLICATIONS

C. R. Brome, J. S. Butterworth, K. J. Coakley, M. S. Dewey, S. N. Dzhosyuk, R. Golub, G. L. Greene, K. Habicht, P. R. Huffman, S. K. Lamoreaux, C. E. H. Mattoni, D. N. McKinsey, F. E. Wietfeldt, J. M. Doyle, 2000, Magnetic Trapping of Ultracold Neutrons, http://dnp.nscl.msu.edu/current/HarvardUCN.html.

I. Lyuksyutov, P. Ball, 2004, Levitating laboratories, http://levitation.physics.tamu.edu/nature_materials.pdf.

I Mogi, K Takahashi, S Awaji, K Watanabe and M Motokawa, 2006, Magnetic levitation experiments in Sendai, Journal of Physics: Conference Series 51 (2006) 431-438.

S. F Savin, L. G. D'yachkov, M. M. Vasiliev, O. F. Petrov and V. E. Fortov; 2009, Clusters of charged diamagnetic particles levitating in nonuniform magnetic field, EPL, 88:64002.

O. A. Kuznetsov, J. Schwuchow, F. D. Sack, and K. H. Hasenstein, 1999, Curvature Induced by Amyloplast Magnetophoresis in Protonemata of the Moss Ceratodon purpureus, Plant Physiol. Feb. 1999; 119(2): 645-650.

\* cited by examiner

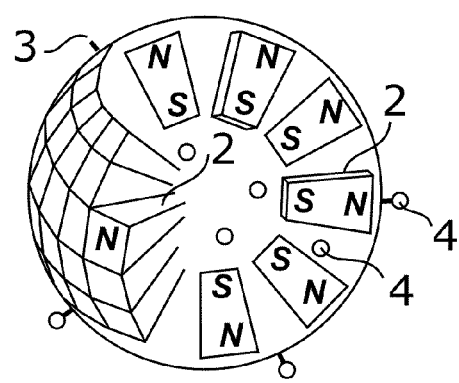
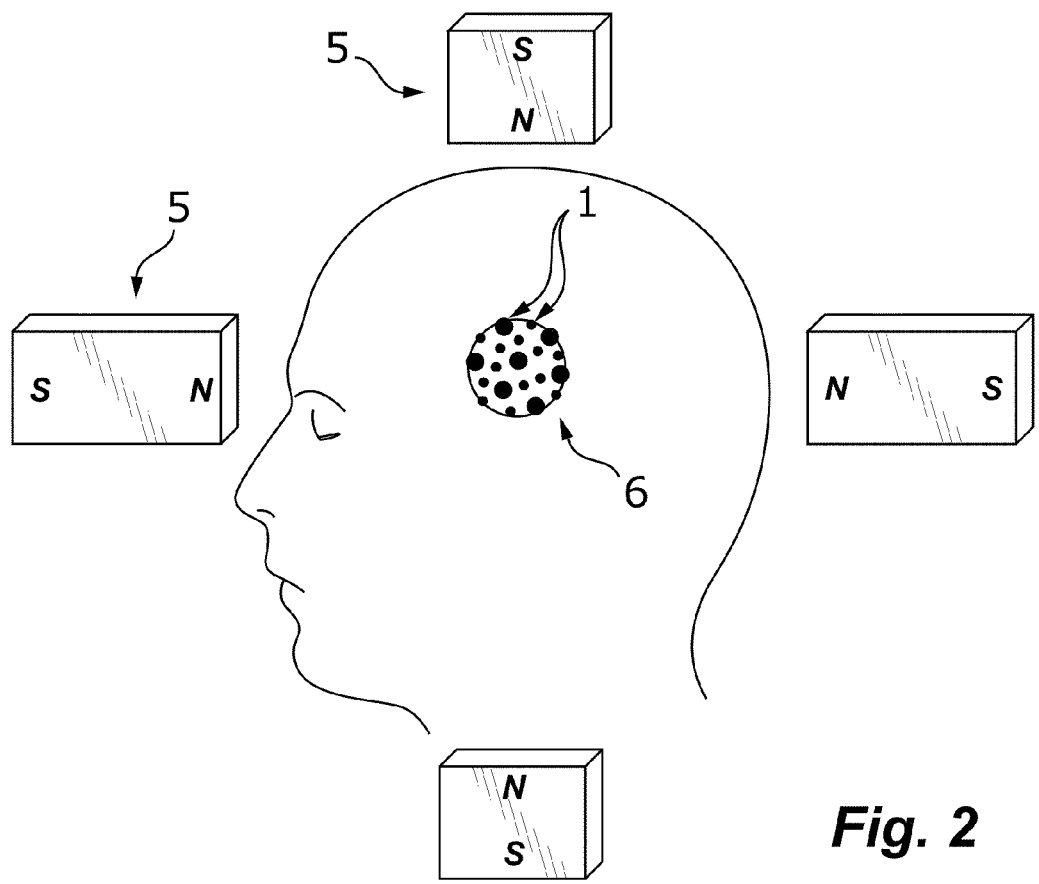
*Fig. 1*
*Fig. 2*

3D TUMOR TARGETING WITH DIAMAGNETIC REPULSION

CROSS-REFERENCE TO RELATED APPLICATIONS

This application is filed under the provisions of 35 U.S.C. §371 and claims the priority of International Application No. PCT/US09/33502, filed Feb. 8, 2009, which in turn claims priority benefit of U.S. Provisional No. 61/032,420, filed Feb. 28, 2008, 61/045,321, filed Apr. 16, 2008, 61/078,434, filed Jul. 06, 2008, 61/082,448, filed Jul. 21, 2008, 61/097,579, filed Sep. 17, 2008, 61/100,865, filed Sep. 29, 2008, 61/106,153, filed Oct. 16, 2008, 61/115,651, filed Nov. 18, 2008, and 61/120,541, filed Dec. 8, 2008, the disclosures of which are each incorporated herein by reference in their entireties.

TECHNICAL FIELD

The present invention relates to the preparation and use of micro and nano particles, particularly medicine-carriers that can be pushed around by magnetic repulsion, for 3D medical targeting.

TERMS

UMC: Unipolar Medicine Carrier or Unipolar Magnetic Carrier. UMC are nano to micro scale magnetic particles, each having a dominating magnetic polarity around its exterior surface, near unipopolar magnetic exterior surface, or even a complete monopolar magnetic exterior surface so that they can be pushed around by a bulk magnet.

DMC: Dipolar Medicine Carriers or particles. DMC are nano to micro scale magnetic particles, can be pushed around by external superconducting Meissner effect and diamagnetic materials, but are always attracted to a bulk magnet.

SMC: Superconducting Medicine Carriers or particles. SMC are nano to micro scale particles, each bear superconductors or diamagnetic materials. They can be pushed around by a hulk magnet due to the Meissner effect.

PMC: Pushable Medicine Carriers, representing UMC and SMC. It may also represent DMC only when the DMC is intend to be pushed around or is being pushed around by magnetic repulsion from a superconductor.

Magnetic repulsion is the repelling force occurs between like poles of magnets, a magnet and a superconductor, and a magnet and diamagnetic materials.

Tiny Magnet: building block of UMC. Can itself sever as UMC.

BACKGROUND OF THE INVENTION

Nano and micro scale particles carrying therapeutic agents and delivered into or within close proximity of the tumor in vivo can play a significant role in increasing the effectiveness of the treatment while decreasing severity of side effects. Such techniques would be highly relevant, particularly, for organs that are difficult to access because of a variety of biological barriers, including those developed by tumors. For example, nanoparticles are capable of crossing the blood-brain barrier due to their small size and thus are an excellent candidate for non-invasive treatment of brain tumors.

The possible clinical use of magnetically guided medicine-carriers for drug delivery to tumors and elsewhere within the body has been studied for decades, but has not become very useful. In fact, the leading company in this field, FeRx Corporation, collapsed in 2005, due to their failed clinical trials on liver cancers, which demonstrated how incompetent current magnetic targeting is, for internal organs.

Conventional magnetic targeting employs magnetic-attraction. It uses DMC (dipolar medicine carriers). Such DMC always align their magnetic polarities to the magnetic field, and are always pulled toward an external magnet regardless of the polarity of the external magnetic field applied. When you pulling such DMC to a target, those DMC in the front move faster because they are closer to the pulling source and those lag behind move slower, and those further behind may get lost, due to the magnetic strength decreases exponentially with distance. The more you pull these DMC, the more they spread over. Tumors close to the skin or a joint might be OK because the skin or joint can stop the spread-over, but deep tumors like those in the brain and liver are not.

There is no way to focus such DMC to a tumor with magnetic-attraction, you have to inject in large quantities; causing the price unaffordable. The second is that the DMC attract each other and may aggregate into a blot, hence blocking the blood flowing in the vessel and causing similarities to strokes and heart attacks. The third is that the DMC are hardly movable, not maneuverable, and cannot be recovered; most of these DMC are left behind permanently in the human body after the treatment, hence causing Ferro liver failure over times, and limiting them for terminally ill patients only. The DMC can only be concentrated below the skin and near a joint, and it has been previously shown that magnetic direction of chemotherapy coated ferrofluid is effective in surface tumors, but it does not work for deep tissue tumors, such as of a depth of 30 cm or greater.

In one word, the conventional drug carriers along with the magnetic-attraction can only do 2-dimensional-magnetic-targeting. 3D-magnetic-targeting is urgently needed but scientists consider it as temping and impossible.

Although artificial unipolar magnets have been invented, such as Herb's toy bail (U.S. Pat. No. 4,874,346) which is built by many magnetic bars that point with their one same poles to the core and the other to the surface, making the whole surface unipolar, we have not found anyone prepared any unipolar particles that are in the micro or nano scale.

We propose PMC (Pushable Medicine Carriers), such as the UMC can be pushed around with magnetic repulsion. As shown in FIG. 4, a hulk magnet, '5', repels a UMC, '1' with its like pole, N pole.

Because the PMC can be pushed around with magnetic-repulsion, they can be used for 3D-tumor-targeting (3-dimensional magnetic targeting or 3D-magnetic-targeting). When you push in-vivo PMC to a tumor with an external magnet, those lag behind move faster because they are closer to the external magnet, and those move in the front move slower, causing the PMC concentrated. You can thus concentrate the PMC as a locus or swamp, push and relocate the locus to different target-tumors, and shape the locus to tumors, for 3D-Tumor-Targeting as shown in FIG. 2, even focus the locus into micro-scale tumors for microsurgeries.

Such 3D-tumor-targeting is very useful: (1) It enables MRI to identify micro-scale tumors and quantities their masses, The PMC can serve as contrast agents for MRI to detect micro-scale tumors so to be able to non-invasively detect tumors at an early stage for maximum therapeutic benefit. For breast cancer, for instance, the goal of molecular imaging is to be able to accurately diagnose when the tumor mass has approximately 100-1000 cells, as opposed to the current techniques like mammography, which require more than a million cells for accurate clinical diagnosis. (2) it enables noninvasive microsurgeries because PMC can be focused to tiny areas with magnetic repulsion. This is the only way to go for noninvasive microsurgeries. And most importantly, (3) it opens the door for therapies to cure cancers, such as for IR-thermal-ablation to destroy tumors (FIG. 5), even micro-scale tumors, and for hyperthermia-treatment to clear up cancer-cells in specific regions. Infrared radiation, '7' in FIG. 5, at 800-1020 nm, will penetrate tissues and heat only the PMC, '1', which, in turn, will heat the cancerous area, '6'. At around 45° C., cancer cells will be killed and normal cells will survive, which is called Hyperthermia treatment. At around 55° C., a tumor will be totally destroyed, which is called thermal ablation. Destroying tumors, including micro-scale ones, one after another can completely clear up the cancer from a patient. The patient will be cured.

UMC (Unipolar Medicine Carriers) will not cause similarities of heart-attacks and strokes; their concentrations are easily maneuverable: you can have a higher concentration in one tumor by pushing them closer together and a lower concentration in another tumor by allowing them to spread over; UMC spread evenly in a tumor; and UMC can be retrieved after a treatment, all because UMC repel each other and do not aggregate.

The invention is good for all kinds of cancers and illnesses, such as prostate cancer, enlarged prostate, brain tumor, liver cancer, lung cancer, etc, you name it.

SUMMARY OF THE INVENTION

The present invention is about using magnetic repulsion for 3D medical targeting. A magnet can push around Unipolar Medicine Carriers (UMC) and Superconducting Medicine Carriers (SMC). A superconductor can push around UMC and Dipolar Medicine Carriers (DMC).

The present invention is also about preparing, isolating, and using PMC, especially the UMC.

In the process of preparing nano and micro medicine-carriers or particles, we will add a step that use magnetic field to control the magnetic-polar-orientation of the material to be added or coated to the carrier, so to make the carrier a UMC.

We will also add a step to prepare medicine-carriers that bear diamagnetic materials or superconductors, so to make the SMC.

We may also convert a normal dipolar medicine-carrier or particle into a UMC. A medicine-carrier may contain many tiny magnets. To convert such a carrier into a UMC, we will re-orientate the tiny magnets in one area of the carrier after another area, until the carrier gets an unipolar or near unipolar exterior surface, and can be pushed around by magnetic repulsion of a magnet. We use energies such as UV or laser to soften or harden the area while using external-magnetic fields to orientate tiny magnets in that area.

We may also convert a solid metal particle or a particle containing demagnetized tiny magnets into a UMC. We will magnetize a small area in the particle, or the tiny magnets within that area, one area after another until the particle becomes a UMC. We use energies such as laser to heat the area to the magnetization temperature or above the Curie temperature while using external-magnetic fields for magnetizing or re-magnetizing.

To isolate the UMC, we use magnetic forces that have the same polarity as that of the UMC. We will apply the force to a container that contains the medicine-carriers to attract dipolar carriers close while pushing the UMC to the farther end for collection.

Pushable-Medicine-Carriers can be pushed around from all directions, which make them very maneuverable. We will use them for 3D-tumor-targeting. They will lead to many cures of cancers

BRIEF DESCRIPTION OF THE DRAWINGS

FIG. 1 is a partial crossing-section view of a UMC.

FIG. 2 shows using external magnetic forces to push a swamp of UMC into a tumor.

DETAILED DESCRIPTION

Properties of Pusheable Medicine Carriers

Figure 3:
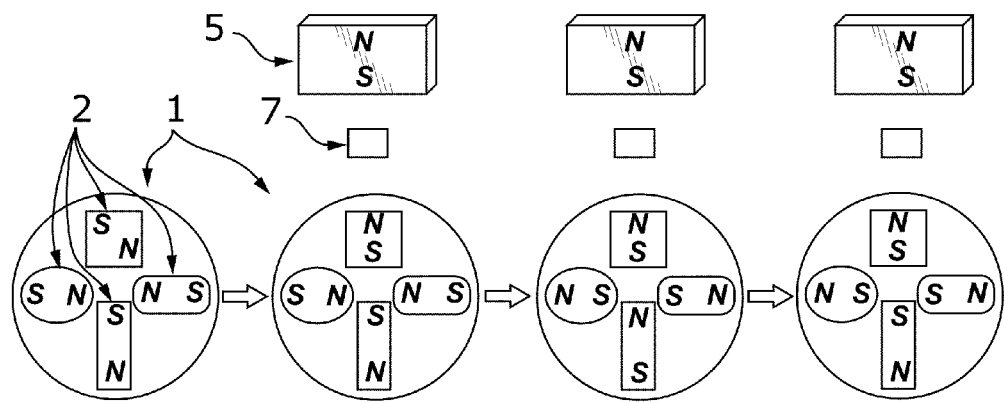
FIG. 3 shows a process to convert a dipolar magnetic particle into a UMC by aligning the tiny magnets in one area after another.
Figure 4:
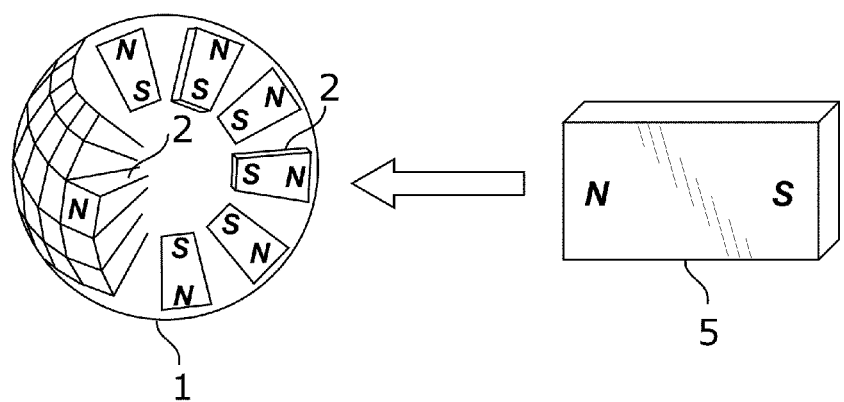
FIG. 4 shows a bulk magnet repels a UMC.
Figure 5:
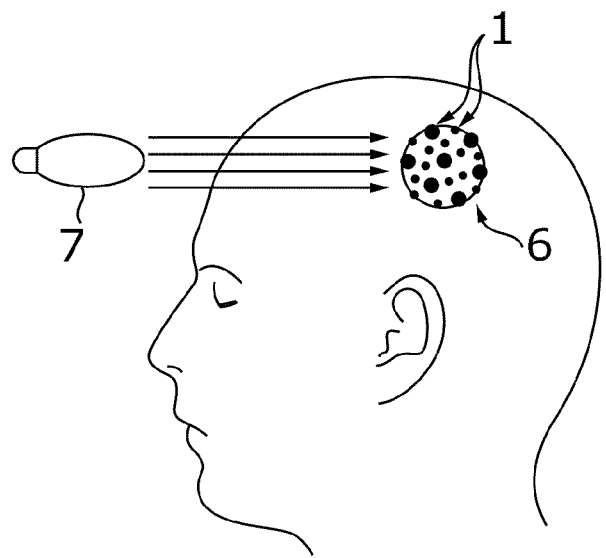
FIG. 5 shows using IR to heat UMC that are already in a tumor.

A typical UMC (Unipolar Medicine Carrier), as show in FIG. 1, is composed of tiny magnets, '2', that point with one common pole (S in this case) to the center and the other common pole (N in this case) to the surface. The particle may have some active groups, '3', on the surface. Medicines, '4', may be tagged to the active groups or contained inside the particle.

A SMC (Superconducting Medicine Carrier) contains enough superconductor or diamagnetic material that can be pushed around by a bulk magnet.

A following description about UMC also applies to all other PMC (Pushable Medicine Carriers), when applicable.

Base materials, such as polystyrene, polypeptides and polynucleotide, may be part of a UMC, for gluing or polymerizing the tiny magnets. The MUC can be in any shape, but preferably as a sphere. The size of the UMC can be any; however, we prefer them to be in the range of 1 nm to 800 microns, The size depends on the uses; such as if we want the UMC to get trapped inside a specific tumor, their size may be 1-2 micron. If we want to push them around in the liver through the hepatic sinusoids that are 2-8 microns in width, their size may be smaller than 2 microns so that they will not be trapped, if we want to push them to go through the interstitial spaces between cells in a tissue, depending on how tight or porous the tissues is, they may be in a homogeneously size within about 25 nm-1 um. If for embolization, the size can be as large as 1200 microns. Through experiments, we will find the specific sizes work for different organs and tissues, and use those specific sized UMC for an organ and tissue. UMC with the size of around 250 nm in diameter can flow freely through both small capillaries as well as blood vessels in and around tumors; we may want that size if we want to push the UMC around through the blood vessels of the tumors. Size in the range 250 nm to 750 micron may go through tumors without much filtration, and we may want these sizes if we want to push around. the UMC in the tumor. Tumor capillaries allow UMC that are as big as 500 nm to get out, due to the EPR (Enhanced Permeability and retention), we will take that into consideration when we concentrate the UMC to tumor blood vessels then destroy the vessels. If we just want to carry some drugs to an area, larger ones such 3 nm-800 microns may be used. If we want the UMC to serve as capsules for use in a gastro intestinal treatment, the size can be much bigger, about 10 mini-meters or so. We will select a specific size works best for a specific use.

The UMC may have a center core, possibly, filled with materials that decrease, shield, or reroute the magnetic forces effectively. An iron-ball may server as the core center in order to buffer the magnetic center, which means tiny magnets can bind all around the iron ball. Mul-metal might be a better choice for the buffering or be used for rerouting the magnetic lines so that the lines will seldom go through to the other side of the UMC, possibly. If we want the tiny magnets to be longer, they may touch each other at the center, and the mul-metal might be put between the tiny magnets. Preferable, the center core does not contain any magnetic material because the magnetic-material, such as the iron-ball above, might get magnetized in a magnetic field and be attracted to the external-magnet, which is not good for pushing the UMC.

Most tiny magnets, if not all, once installed to the UMC, point with their south poles to the center and the north poles outward to the exterior surface, or vise versa. We prefer the size of the tiny magnets to be 1 nm to 800 microns or, even 1 to 30 nm, as such sized magnets are single domain in their magnetic moments. The tiny magnets can be in any shape, such as a ball, a bar, a rod, etc. The tiny magnets are either bare or coated with some materials.

The base-materials that hold the magnets may also be those materials that reroute the magnetic force effectively. We prefer not to use the base material to cover the end of the tiny-magnet that faces the surface of the UMC. However, if we have to submerge the whole tiny magnets inside the base materials, for any purpose, the layers that cover the surface polar end of the tiny magnets should be as thin as possible.

The outmost layer may be a hard coating, such as a SiO2 coating. It may also have specific properties, such as when we want the UMC to stick onto the hydrophobic cell membrane, the outmost layer, if hydrophilic, may melt away in time so to expose the inner hydrophobic layer.

The UMC may have multiple tiny-magnet layers or shells. Different layers may have same pole or different poles point outward, such as the inner layer pointing with its south pole outward and the outer layer pointing with it north pole outward, or both layer points with their north pole outward.

The tiny magnets in a particle may not be in a shell or layer. They can be very unevenly reside in the medicine carrier, some regions may have more and some regions may not have any, some regions may have multilayer, some regions may have a few or none, as long as their magnetic orientations make the particle behave like a UMC, can be pushed around with magnetic repulsion of a magnetic field.

Each UMC may contain many different kinds of base materials. Base materials may change status upon receiving or releasing some energy. Once changed, the new status may allow or disallow the tiny magnets to change their orientations. Such base materials may be used in the UMC to glue or hold the tiny magnets.

The UMC may contain or associate with all known medicines, such as drugs, Boron (10), heating medium, radiation or other signal moieties. The medicines can be put inside the UMC or tagged at the surface. In addition, the UMC may be labeled or tagged with positrons or any signal moieties such as indium-111, for positioning purposes or viewing them inside the body with some machines.

Preparation

In the process of manufacturing, synthesis, preparation, making or producing nano to micro magnetic-particles or their components and intermediates, we propose to add a step, effort, means or procedure for the purpose of knowing, controlling, aligning or taking care of the magnetic-polar-orientations of the tiny magnets or materials that are to be incorporated, installed, added, or coated to the particles, such as a means to let us know what direction the north poles are pointing to, etc. In another word, old manufacturing process does not care the orientation of the tiny magnets but we do and we will have a step to monitor it, such as we may apply a strong magnetic force(s) from one or more directions to the container that contains or holds the tiny magnets. The force(s) may overcome the interactions among those tiny magnets and make them point their north pole to one direction. That means we may use magnetic field to magnetize the magnetic material or orientate the tiny magnets before, during, and after the modification of the tiny magnets.

The added step may use magnetic field to align or orientate the tiny magnets in a particle, during the installation of these tiny magnets to a particle or, if they are already in a particle, it wilt use the magnetic field to orientate the tiny magnets to the right polar. The magnetic field is used as an orientating means rather than just as a testing means. The step orientates tiny magnets in a specific region in the particle, one region at a time, and one region after another. It then fixes their orientations by changing the status of the base materials, The added step will not use mechanical means that touch each tiny magnet to orientate the orientation. All means other than the mechanical means may be used, in similar ways as the magnetic field, to take care and ensure that most tiny magnets face their one common pole outwards and the other to the center. In case that the installed tiny magnets are not originally magnetic, the means will ensure they will be magnetized or re-magnetized in that way. Further more, in case the medicine carriers are prepared directly with magnetic materials, the means or steps will ensure the carriers get magnetized or re-magnetized in that way.

First embodiment for preparing the UMC: put the tiny magnets against a membrane; apply some magnetic forces that are so strong to overcome the interactions among the tiny-magnets so that they will stand with one same pole facing to the membrane. The magnetic field may be applied from the bottom side of the membrane. The tiny magnets will bind to the membrane. Then the membrane are cut into small pieces with some technologies, the small pieces will be heated or cooled so to allow the membrane to contract so to form the beads with tiny magnets around.

Second embodiment for preparing the UMC: to a colloid solution containing the tiny magnets, we add a layer of oil or organic solution, and then put a strong magnet to draw the tiny magnet into the layer. The layer is not so thick so that the other pole of the tiny magnets will stay in the solution. We may then modify that pole, such as we may add active groups that allow the tiny magnets to bind to a medicine-carrier with that specific pole, or bind together with that modified pole, and after they bind together we add polymers to the bound the tiny magnets. The tiny magnets may be coated with magnetic shielding material all over. If the whole tiny magnets or tiny superconductors are coated with the shielded materials, for the purpose of avoiding them interact with each other during the preparation of the medicine-carriers, we may, when necessary, clean up the shielding materials from the poles that face the out surface once they are installed into the carriers.

Third embodiment for preparing the UMC: the particles or medicine-carriers are not original magnetic or they are demagnetized. They will be magnetized or re-magnetized into UMC. Such as, after the particles are prepared, we put them into a container. Around the container, we put high magnetic forces or surfaces that with one same pole points to the container. We may then increase the temperature to a specific degree, let the particles get magnetized. The surrounding magnetic forces may be put in a specific way to make the particles unipolar. Then, we cool down the temperature to retain the magnetism permanently. The surrounding magnetic forces or surfaces may be applied to the container one after another, not at the same time.

The third embodiment may also include another way to make the UMC. Once the non-magnetic particles are prepared, we add to them magnetic particles that are much smaller. The smaller particles have only one pole can magnetically bind to the big particles, the other pole is modified such as coated. As the big particles are ferromagnetic, many smaller particles will bind on the surface of each big particle; we then change the temperature and/or other factors to make the big particles magnetically unipolar and permanent. Other than using small particles to bind to the big ones, we can cover the surface of a big one with unipolar magnetic materials or sheet, then change the temperature. The smaller particle or sheet should have a higher Curie-temperature than the big ones, and we heat the complex to the Curie temperature of the big ones.

Forth embodiment fir preparing the UMC: The particles might be mesoporous and have V shaped holes. The tiny magnets have V shaped south poles. Both the V shaped holes and the V shaped south poles have hydrophobic groups so that the pole can get into the hole and bind there. Other than the hydrophobic groups, we may use chemical bounds, active groups, electric charges, enzymes, and DNA or RNA specific sequences and so on.

When the activated pole of the tiny magnets is hydrophobic, the particles will have hydrophobic regions on the surface to allow the activated pole of the tiny magnets to bind to. When the activated pole of the tiny magnets has chemical bounds or groups, the surface or regions on the surface of the particles will have corresponding chemical bounds or groups that will bind or react with those on the activated pole of the tiny magnets so to allow them to bind to the surface. When the activated pole of the tiny magnets are electrically charged either positively or negatively, the surface or regions on the surface of the particles will have negative or positive charges that allow the oppositely charges on the pole bind to. If the activated pole of the tiny magnets have specific antibodies, antigens, ligands, or receptor, the surface or regions of the surface of the particles will have antigens, antibodies, receptors or ligands that allows the antibodies or antigens on the activated pole to bind to. When the activated pole of the tiny magnets has DNA or RNA with specific sequences, the surface or regions of the surface of the particles will have DNA or RNA having sequences that are complimentary to those sequences on the activated pole so to allow the hybridization to happen to allow the binding, etc.

These chemical bounds, active groups, electric charges, enzymes, DNA or RNA specific sequences may be on the tip of long arms, and the long arms will retract in length at difference physical conditions like different temperature, PH value, etc. or when treated with some physical, chemical, biochemical agents. Such as a specific DNA sequence can be at the top of a DNA arm. The specific sequence will bind with its complimentary sequence, once in cold condition or be treated with UV for crossing linking, the DNA arm will bend or retract in length so to draw the tiny magnets closer to the surface of the particles.

Tiny magnets conjugated with DNA may serve as construction unites. To make such construction unites, we may pull a layer of the tiny-magnets to a bulk magnet surface, put the layer into a solution containing oligonucleotides or single strained DNA, let the DNA to attach to the surfaces of the tiny magnets that are exposed to the solution, add big particles that have cDNA regions that are complementary to the single strained DNA, let the attached single strained DNA to hybridize with their cDNA regions on the big-particles, and fix the resulting complex by methods such as by UV DNA crossing linking or materials such as other polymers that can till the empty spaces. The complexes come out from the above process will be released from the magnetic surface then added to another solution that contains same layer of conjugates. Repeat the above process to make unipolar magnetic nano or micro particles. As each big particle has multiple cDNA-regions all around its surface, it will bind to multiple DNA and tiny-magnet-conjugates around its surface. The big particle can be made by all different materials such as DNA, protein, polymers and organic or in-organic materials.

We may use a big magnet to pull a layer, or not a complete layer or multiple layers of tiny magnets to its surface then put base materials to fix and stick the tiny magnets together into a complex, then grind the complex into breakages with desired sizes. We may use these breakages as building blocks to build the UMC. The breakages may be modified to have electrically charges, to have a hydrophobic/hydrophilic surfaces, etc so to prevent them to aggregate together. They will be further modified to allow only one pole to bind together or to a big particle so to form the UMC.

This means we use those tiny magnets that are activated at one common pole as construction unites. In order to make one pole of the magnets special, other than the means mentioned elsewhere, we may use solid support mean such as we may use a strong magnet to absorb all the tiny magnets to its surface. The surface may have a layer of hard staff in front the magnet. The surface can be smooth or may have many holes. The surface may further have a layer of materials, such as wax or oil, that may submerge the selected pole and prevent the modifying chemicals or means to assess the submerged portion, but expose the other pole to allow the modifications. We may also put some modification mechanisms, such as some modification chemicals on the solid surface or in the lay of materials, such as the above mentioned wax, to modify the pole that are attracted to the solid surface of the strong magnet. As the tiny magnets be attracted to the surface with a common pole, we may treat that pole or the other pole to make either special, For example, we may clean up one pole of the SiO2 coating that are produced by Yamamoto's method (Yamamoto, et, al Appl. Phys. Lett. 2005, 87, 032503) or remove the anionic charge synthesized from Massart's method (R. Massart, IEEE Trans. Magn. 1981, 17, 1247). The other pole will not be modified such as they will still have the coating and anionic charge for the binding to the beads or medicine-carrier. We may use these activated tiny magnets for preparing medicine carriers with the method described by Dobson (United States Patent Application, publication number 2006105170 with filing date May 18, 2006). We may also modify Chen's method (U.S. Pat. No. 7,081,489) by treating only one pole with an anionic surfactant to form modified active tiny magnets. While one pole is activated, we may also protect the other pole by coating or any other means so to protect that pole from binding.

The fifth embodiment for preparing the UMC: The tiny magnets are unipolar themselves and may be directly used as the UMC We may make the unipolar tiny magnets in a unipolar magnetic field. The tiny magnets, such as a $Fe_3O_4$ balls, are heated to a certain degree. Unipolar magnetic fields are applied from all directions, or specific directions, to the tiny magnets, which will make the tiny magnets unipolar, then they are cooled down to get 'frozen' in the unipolar status. We may install these remnant unipolar tiny magnets to the particles.

Here is just an example about how to prepare the unipolar tiny magnets. Metal wire is constantly being inserted into a channel. At certain location, the wire tip is heated by some heating means such as fire to a high and selected temperature. The tip gets melted. Strong gas, such as air, N2 or O2 is blowing to the tip to blow away the melted metal as small metal-drops and the drops get into the channel that have unipolar magnetic field either around the channel or on all directions. The drops will keep turning so that their surfaces get unipolar magnetic. Then the drops get into a section in the channel or another compartment, either having the unipolar field or not, but is very cold. The metal-drops are quickly frozen into solid drops with remnant unipolar magnetism. We may control the size of the magnets by the speed we put in the wire, the diameter of the wire, the temperature to heat the wire, and the speed we blow the gas. The gas should be strong, possibly around the wire, blowing in the direction to let the metal drops stay in the center of the channel, and let the drops to get into the cold part and freeze into solid before the drops contact the wall of the channel.

The unipolar tiny magnets can be made bigger; can be 30 nano to 800 microns, so that only one or a few of them get installed in/on each medicine-carrier. Or only one or a few get covered with or attached to some materials so to make a medicine-carrier. They may serve as the cores of the medicine-carriers and are stabilized by an organic shell.

Here is an example for how to make a UMC that has already incorporated those dipolar tiny magnets. The tiny magnets may be held together into a polymer or any other holding materials. We may change the physical condition of the particle such as heat it to a temperature that the holding materials become soft and the tiny magnets can turn in directions. This can be done by heating the medium, such as water, that contains the particles. We apply unipolar magnetic field around the particle or just around a channel like we do above. As the particle turns while passing the channel, the unipolar field will turn the direction of the magnets to make the particle unipolar. The particles enter into a medium such as very cold water to quickly cool down so to make the holding material hard again to fix the magnets, which will make the particle unipolar.

The sixth embodiment for preparing the UMC is shown in FIG. 3, where, a microsphere, '1', contains tiny magnets, '2'. A laser-heater, '7', heats and softens the top-area of the microsphere and, a Magnetic-Source, '5', using its S pole to orientate the tiny magnets so to make them point their N poles outwards. See the 'best mode for preparing the UMC'.

There is a new technology for heating which is to use nano or micro wires that get heated to exact temperatures by controlled electric currents. The electric current in the wires will attract the particles to contact the wires, and the heated wires may heat the specific area of the nano or micro particles that contact the wires.

This embodiment uses energies to soften the base material. Similarly, we can harden or cure areas that are already made of soft materials that already allow tiny magnets to orientate. Such as, we may mix tiny magnets with UV-cured acrylic-based resin, then pour the mixture into a medium that can suspend the resin, then stir it so that the mixture will turn into small particles, and the size of the particles can be managed by the speed of the stirring, then apply UV and magnetic force from a same direction as the UV to the small particles in the medium. Because the tiny magnets in the resin can turn, the magnetic force will align the tiny magnets. The UV will only cure the exposed area in the particles that face the UV so that the tiny magnets get fixed when the resin in that area is cured. As the medium is being stirred and the particles are spinning and moving up and down in the medium, overtime, every area of the particles will be cured and most tiny magnets in the particles will be fixed in the way that the particles are unipolar.

We may coat the particles with a hard shell made of other material, such as biocompatible polyethylene glycol, gold or $SiO_2$.

The material that makes the hard shell should stay hard at the temperature at which the base material softens. The hard shell is multi-functional. It may be used for keeping the particle in shape when the base material is softened. It can be a $SiO_2$ coating. The $SiO_2$ coating allows the IR-heating-beam to go through. It has a higher soften-temperature than the base material such as polypropylene so to prevent the tiny magnets from getting out of the microspheres during the above process. We have recently spoken to an expert in lighting, he said the $SiO_2$ can be further engineered to contain special structures or dyes so that it will allow IR radiations that come straight to the microsphere to enter, and IR radiations that comes in certain angles will be weakened or blocked. We will try that suggestion if it turns out to be a must.

Free-radicals that polymerize or harden the softened area at specific temperatures may be added into the mixture or base material to increase the soften temperature of the region, so that, next time the region is heated, it will not soften again. Free-radical materials that get activated upon UV or other irradiations may also be used directly in the process of orientating and fixing the tiny magnets.

Many forms of energies can penetrate the particles. We need to add some dyes or any other materials that can block the energies from penetrating the particles and allow only the desired region get cured or softened. Also the strength of the energies such as the wavelength of UV or any other light should be carefully selected so that it will cooperate with the dyes to penetrate only to the desired depth of the particles. The medium may also need some materials to manage the penetration so to, for example, quickly absorb lights or energies that are reflected by the particles.

It is not so critically but just in case we find IR-dyes that are unstable to ultra-violet (UV) irradiation as described at wikipatents.com/gb/2173914.html, we will use them in the particles so that we may apply both IR beam and UV beam to the particles during the transformation to UMC process. The UV beam will destroy the IR dyes so that they will not absorb much IR energy after the first exposure, which will ensure the finished areas in the particles stay unchanged.

Rerouting or shielding the magnetic lines of the external magnetic sources may help the above process. Shielding material can be anything such as good magnetic conductors, paramagnetic, ferromagnetic, diamagnetic and/or superconductors, etc.

All known materials that can change physical, chemical, and/or biochemical properties under different conditions may serve as the base material or the matrix in the UMC, such as Epoxy based electron beam (EB) or UV curable systems such as epoxy cationic polymerization materials, acrylic Glue, synthetic temperature sensitive polymer, namely poly(N-vivyl caprolactam, polyacrylamide, polyacrolein. polyvinyl alcol, co-polymers N-isopropylacrylamide, methacrylic acid, poly ethylene glycol derivatives, as well as natural polymers such as starch, alginate, chitin, chitosan and derivatives, cellulose, etc. Biologic materials, such as DNA or RNA can cross link under UV so to turn hard to fix the magnets, proteins can denature under certain energies such as when get heated it will turn hard, and starch can turn into carbon hard material, can be used as the matrix or be added to the matrix. Some resins, being used in the printing industry can be cured in milliseconds, may be the best choice for the base material.

Electron beam (EB), neutron beam, positive or negative charges particles alpha, beta, gamma and all other radioactive radiation energies, Ultraviolet, infrared, visible light and all other lights, laser, ultrasound, sonic sound, direct heat, pH values, special chemical, special enzyme, chemical oxidization/reduction, cold plate in hot solution, hot plate in cold solution can be used to serve the role as the UV does in the above approaches. All these are called energies and all other forms of things and agents, such as enzymes, that can be used to change physical, chemical, and/or biochemical properties of base materials, such as condition from one status that allow or disallow the tiny magnets to change their orientation to another status that disallow or allow the tiny magnets to change their orientation, will be considered to be used as energies for this invention.

The energies should change the status of the base material in a specific region of each particle, region by region, the energies may be applied from one or more specific directions, for a specific length of time such as for less than a millisecond to a long time on each flash, and with specific strength in Watts/CM and/or wavelength as may be measured for that specific energies.

The energies, lights, and the magnetic force may be applied to the particles in pulsate manner, and or oscillated manner, and, from opposite or different directions at a time, to coordinate the application of the magnetic aligning forces. They may also be applied from all directions at the same time. We may certainly apply another magnetic field with opposite pole to the particles in the medium at the other side to help the alignment, without the energies such as the UV.

The magnetic fields '5' in FIG. 3 may come from magnets, electronic magnets, or magnetized superconductors. They may he applied to the particles in a constant manner, pulsated manner and/or oscillated manner to coordinate the application of the energies that change e status of the base materials. Rerouting of the magnetic fields may be used.

The application of the magnetic fields and energies are controlled in exact times, so to allow only the desired regions in the particles to change the status and in the meaning time the tiny magnets in those regions finishing changing their orientations, and then getting fixed in desired timing.

Here is the seventh embodiment for preparing the UMC. The above methods align and lock permanent tiny magnets one region after another to make unipolar particles. In a same manner, we may magnetize or re-magnetize tiny magnets that are already in a particle one region after another to form unipolar particles. The tiny magnets are already installed and locked in a particle. They cannot more or orientate any more. We may heat one region of the particle, in the mean time apply magnet force to the particle to magnetize the tiny magnets, then cool that region down to 'fix' the obtained magnetism, one region after another, until we get the UMC, The temperature used should be low not to cause the base materials softened but high enough to cause the tiny magnets to gain and retain the desired magnetism.

The seventh embodiment may also convert a solid particle such as Neodymium (or any other metal) particle into a UMC. The heated region of the particle gets its magnetism from the magnetic field, '5' in FIG. 3, and then the region is quickly cooled down, retaining the obtained magnetism, When all the necessary regions of the particle obtained and retained the magnetism, the whole particle becomes unipolar.

Here is the eighth embodiment for preparing the UMC, which polarizes a defined small area of a particle by controlling the magnetic material to be or being added or coated to that area, through a magnetic field. We will use double-layered-disc-like particles to serve as the UMC. Such disc-like-UMC, '1' in FIG. 6, has two layers that point their one common pole, N pole, to the outside surface and the other common pole, S pole, to the center between them.

The 'gas condensation' method uses heat to evaporate metal in or without a vacuum then collect the metal molecules on a cold collector to prepare nano or micro particles or membranes. We may use this process to evaporate then collect any materials or complexes. All materials, such as rare earth element Neodymium (Nd) and ferro-magnetic metal Fe, Co and Ni or any others, complex or alloy such as iron-nickel alloy may be used, and may result in permanently magnetic layer membrane to form on the collector with the use of external magnetic forces.

We use the heat to evaporate metals such as Neodymium, add magnetic forces to the cold collector and collect the metal, stop for a while, reverse the polarity of the magnetic force, start to evaporate the metal again, and collect another layer of the metal. If we do not want to reverse the magnetic polarity, we may reverse the collecting membrane. We may peal up or take up the first layer of metal that we collected, possibly along with the membrane that collect the layer, and put the opposite site of the layer to the side for collection then collect the $2^{nd}$ layer.

The temperature and all other parameters should be controlled in a way that permanent magnetic moment will be put on to the resulting layers, and a person skilled in magnet manufacturing might be good enough to provide the help. The magnetic force added to the process may be vertical to the collector, letting the collector collect one layer of particles or membrane, then, reverse the polarity of the magnetic force and collect another layer.

This process will make double layered magnetic particles, with a single common polarity, say N pole, face to both out-surface, and the other pole, say S pole, face to the center between both layers.

Figure 6:
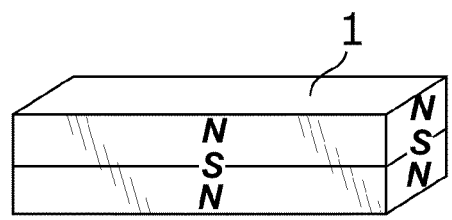
FIG. 6 shows a double-layered-disc-like particle, with N polar points to the external surface and S polar to the center.

In case of nano-membrane, we may then break the membrane into small micro or nano scale disc like particles, see FIG. 6. There are many methods, such as by grinding, to break a big magnet into micro or nano particles. All the methods will be evaluated and tried for our purposes.

We may avoid the break down step by using some other technologies such as photoliphoperaphy, or applying a layer of chemicals to the collector. The layer will have grids that bump up so that when the membrane is forming, the grids cut the membrane into the preferred sizes. We may then pill up the membrane along with the chemical or simple dissolve the chemical layer and the grids with some special solvents, and then collect the double layered particles. The layer can just be some kind of plastics that can be easily dissolved with acetone.

Nanocoating can go in the same ways as above, where coating one layer with a external magnetic field then coating another layer with reversed orientation/polarity of the external magnetic field to get the above double layer or disc like particles.

The magnetic field(s) added to the manufacturing environment may be multi-directional and with specific strengths and applied with specific timing, so that the resulting products may each has multi-directional magnetic polarities and each has desired strength. The magnetic field applied during applying the second layer may be stronger so that it overcomes the magnetic field and the thickness of the first layer, and give the second lay identical strength of magnetism as that of the first layer.

Before collecting the second layer, we may also add a layer of different materials to the first layer. The added layer may serve as buffer for the magnetic field, may be stronger to bind both layers then they bind themselves, or may be for any other purposes.

Figure 8:
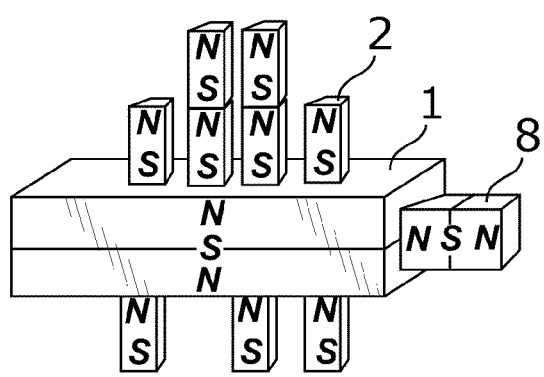
FIG. 8 shows more tiny magnets get to the surfaces of the disc like particle.

Further more, we may add small tiny magnets, '2' in FIG. 8, to the disc-like-UMC with a certain ratio. After we obtain the disc-like-UMC from the above process, we may mix them with tiny (nano or micro) permanent magnets in a medium, and stir the medium. The speed of the stirring, time of the stirring, and the temperature and other environments will be controlled. The tiny magnets may be big enough so that they will not bind to the center S region, due to the pushing from N regions at both outmost-layers. The tiny magnets will bind to the disc-like-UMC, with their S poles face to both N polar surfaces, and, with many layers at the center and fewer layers when getting to the edge and one single layer at the edge. The added tiny magnets will align with the magnetic field of the disc-like-UMC. We may use stirring forces to control the layers. Such bounded disk-like-UMC may be magnetically unipolar, because they may behave like a unipolar magnet in a magnetic field due to the thermal motions may overcome the S polarity force comes from the center between both layers.

The size of the tiny magnets can be any such as 30 nm, The size of the disk-like-UMC may be any from 30 nm to 800 um.

Each disk-like-UMC has a small S (or N) region exposing outside between both layers. We may anneal this region with smaller disk-like-UMC, '8' in FIG. 7, each of which is much smaller in size, otherwise identical with the bigger disk-like-UMC. These smaller disk-like-UMC will bind to the S polar region of the bigger disk-like-UMC with one of its N pole and then point its other N polar outwards, forming an annealed disk-like-UMC which is better in terms of unipolarity.

We may coat the disk-like-UMC, the bounded disk-like-UMC and the annealed disk-like-UMC with polymer(s), SiO2, or any other materials. There are many ways for the coating, and we will try every one for our purpose. Once coated, they will serve as good medicine-carrier for magnetic targeting. Such disk-like-UMC can be pushed around by external magnetic forces, diamagnetic material(s), and/or superconductors. Each drug-carrier may contain one or more of them.

The nano-membrane may have many layers, with different magnetic polarities in different layers.

Figure 7:
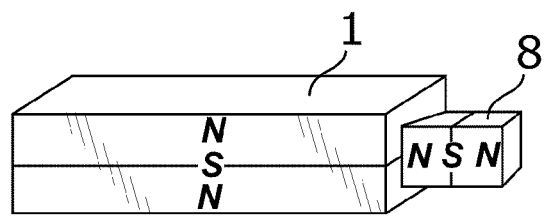
FIG. 7 shows the disc-like particle get annealed by a smaller doubly-layer-disc-like particle at the center.

We may also use metal molecules or ions to replace the tiny magnets, '2' in FIG. 8, and use the anneal magnets, '8' in FIGS. 7 and 8, to grow or anneal the double layer particles.

Here is our ninth embodiment for preparing the UMC. We use tiny magnets to make the disk-like-UMC. In a medium that contain tiny magnets, we apply to the wall of the container magnetic force which is unipolar, say S unipolar. The tiny magnets will be attracted to the wall with their common N poles. We may stir the medium so hard that the tiny magnets may bind only one layer to the wall. To ensure only one layer, the concentration of the tiny magnets in the medium must be determined. The wall may be pretreated with chemicals to bind the tiny magnets together, or we may now add chemicals that can bind them together and bind them to the wall. Then we may reverse the polarity of the applied magnetic field, making the N pole face the medium, and with stronger strength that will overcome the magnetic filed of the first layer and the thickness of the first layer, so that the second layer will get the same magnetic strength. We then add to the medium tiny magnets, may be as many as we added for the first layer, so that the newly added tiny magnets will bind to the first layer with their common S poles to the first layer. We may add more chemicals to bind them together. We will peel the membrane then break them down to the disk-like-UMC. The wall may have a membrane to help the peeling.

We may combine our inventions with methods used by other people to prepare many more different kinds of UMC. For example, there are two possible processes for manufacture of high energy anisotropic Neodymium based rare earth magnets. One process uses melt spun isotropic crushed ribbon, hot pressed and plastically deformed. which results in domain alignment and anisotropy. This process is still in the development stage. The other process being used widely is a classical powder metallurgical process used by AMS. Cast alloy slabs, produced from molten alloy of the right composition that are crushed mechanically to minus 3 mm in size and then milled to 3-5 µm powder. The powder particles are magnetically aligned in an electromagnetic coil then pressed to shape in a mechanical or isostatic press. The pressed compacts are then sintered at 1100° C., finished to size by grinding or slicing, and magnetized in an electromagnetic coil at a very high magnetic field. Whilst the basic process appears simple, in practice very strict controls at every operation must be maintained. Powder of the alloy is extremely pyrophoric, bursting into flames in contact with air. All operations must be carried out under inert atmosphere. Even a minute presence of oxygen will render powder useless. Other important parameters are particle alignment, particle size distribution and sintering parameters. We may these methods with our inventions, using the powder to make the UMC. The powder may be milled to the size we need, demagnetize the powder if necessary, and then use our methods to convert the powder to the UMC.

Here is the embodiment for preparing the SMC (Superconducting Medicine Carriers). We make the SMC by methods published for preparing nano and micro particles but with superconducting or diamagnetic materials as the major material. Those methods include the up down methods that grind a bulk superconducting material to nano or mircoparticles with grinding systems, and the bottom up methods that use chemical reactions to put superconducting materials together into nano or micro particles. Once the SMC are made, we may coat them with gold, SiO2, thermoplastics, or any other materials. Such as we may put some SMC and some polypropylene into water and heat the water to 180 degrees C. under high pressure so that the water will not evaporate. We may then shake the container so that the high temperature change the thermoplastic into droplets, suspended in the water and take in the SMC. Once we cool down the water, the SMC will be coated by the thermoplastic, and thus we get particles containing the superconducting material. In a similar way, we can prepare particles containing diamagnetic material. In case of superconducting material is used, the particles that made off or contain the superconducting material will be turn into the superconducting state before, during, or at a specific time when they are used for medical targeting. The particles should contain enough superconductor or diamagnetic material so they can be pushed around by a bulk magnet.

When using external superconductors as the pushing source, the magnetic medicine-carriers can be unipolar or dipolar. They can also be paramagnetic or ferro-magnetic. When we use dipolar nano or micro carriers, we need to keep the carriers from aggregating. We may use smaller carriers so that their thermal excitations, such as the Brownian motion, can keep them apart at our body temperatures. We may also modify the carriers by coating with good materials, such as SiO2, or adding charged groups, either positive or negative, to their surfaces, such as $COO^{-2}$, to prevent them from aggregating. Charged groups can avoid these carriers binding to each other.

Such modifications are also for other purposes. Negatively charged carriers are less likely to be eaten by lymph cells than positively charged ones, and we may use such changed to control the interactions of the carriers with in vivo cells. To evade the immune system, we may add some lyses to the surface of the particles to break the immune cells once they are captured by those cells.

The added groups should be able to change their properties upon receiving some treatment such as some agents. The modifications may be carried out at higher temperatures at which the carriers will not aggregate, or before those carriers get magnetized and, in which case, we will magnetize them after the modifications.

Best Mode for Preparing the UMC

Specific Aims

Prepare the UMC, and show the UMC are feasible for 3D-tumor-targeting.

Special Terms:

heating-time: The length-of-time of each heating, with pulsed-laser. Each heating will ideally soften 200 nm deep into top-areas of microspheres exposed, or heat that area to the magnetization temperature or above the Curie temperature of the tinny magnets we are using.

interval-time: The length-of-time laps between each heating, allowing the melted or softened top-areas to get back hard or the heated tiny magnets to cool down, in the presence of an external-magnetic-field the bulk-magnet in FIG. 3)

Materials:

1. Fluorescent-Microscope (Olympus BX61) with resolution 10-15 nm, may he purchased from Scientific Equipment Group; Laser-machine: may be purchased from http://www.newandusedlasers.com/, www.northeastlaser.com or any other sources. Possibly with specifications: Wavelength: 808+/−10 nm, Output power: 0.05-6 KW, Beam dimension: 12×12 mm, Pulse Duration: ps to sec, We may go to their laboratory or they may come to our laboratory, for them to demonstrate their laser machine can soften 200-2,000 nm into a solid plastic. We will use a microscope if necessary. It is not critical but just in case the vendor can make it, we will have a. Laser-machine that provides thousands or millions of separate laser beams. And the machine allows us to adjust the beam-focus-size or beam-dimension, such as to 250 nm, so that a beam can soften only the top area of a microsphere, when the top area happens to get right inside that beam, if not right inside, the beam is not strong enough to soften any area.

2. Microspheres: May be purchased from Phosphorex, Incor SoluLink—The Conjugation-Company, in San Diego, Calif., USA, or any companies as listed: http://www.magneticmicrosphere.com/suppliers/magnetic_microspheres.php We need two types of microspheres:

(2a) The $1^{st}$-microspheres are made of ferromagnetic, preferably Neodymium-tiny magnets, co-polymerized with polypropylene, and are coated with a 50 nm layer of SiO2.

(2b) The $2^{nd}$-microspheres are made by the Core-Shell method, which means they have a hard-core, The hard-core is about 1400 nm in size, being made of SiO2 without tiny magnets. The hard-core will contain heavier IR-dyes to block the laser-beam from passing through. Around the hard-core is a 300 -nm-thick-layer made of neodymium-tiny magnets co-polymerized with polypropylene, etc. And, the outmost is a 50 -nm-thick-layer of SiO2 coating.

The neodymium tiny magnets may be in the high-temperature grades that retains their magnetism below 200° C. The low temperature-grade that retains magnetism below 80° C. will work here too, using other sterile methods, such as ethanol treatments, to replace autoclaving for sterilizing the microspheres in the clinic. The tiny magnets may be demagnetized ones, if so, may be installed in the right orientations and may not need to be copolymerized with polypropylene, etc. The nanomagnets should be about 200 nm in size, and should be cone-shaped with the wider end having the surface polarity of the UMC. Although all different shapes will work, the cone-shape might work better, to let the laser energy easily soften the surrounding polymers when the tiny magnet is not in the right alignment, and, when getting to the right alignment, the tiny magnet will block the laser beam, like an umbrella, to prevent softening its surrounding polymer. The tiny magnets will be labeled with fluorophore (fluorescein or DyLight 488).

This $2^{nd}$-microsphere may simply be whole ferromagnetic or neodymium nano or micro particle, possibly demagnetized, without containing any polypropylene, when we determine it is necessary.

The polypropylene is a thermoplastic-polymer which is hard and rigid below the softening temperature of 145° C., and melts at 160° C. It can withstand autoclave normally at 121° C. It is with poor impact strength below 9.50° C. but we will use it at the body temperature.

The microspheres should further contain Near-IR-absorbing-dyes, Epolight-4149 (Epolin, Inc. Newark, N.J., USA) is a good IR-dye. It contains biocompatible components MEK, Xylene, and Cyclohexanone. We will have a high concentration of it in the microsphere, so that the IR energy will be exhausted only 200 nm into the microsphere. We will ask the company who prepare the microsphere to add the dye in 5 different concentrations (grams of dye/100 grams of polypropylene): 0%, 0.1%, 0.5%, 1%, and 5%. The concentrations are subject to the recommendations from the vendor of the IR machine.

It is not so critically but just in case we find an IR-dye that is unstable to UV irradiation as described at wikipatents.com/gb/2173914.html, we will use that dye in the microsphere. We may apply both IR and UV to the microspheres during the UMC-preparation. The UV beam will destroy the IR-dyes in the finished area, so that the finished area will not turn soft again upon further exposures to the IR, ensuring the finished areas in a microsphere stay relatively stable.

3. Magnetic-field-generating-equipment is commercially available for generating controlled applied magnetic fields in the many-Tesla range. One example is available from Cryomagnetics, Inc. A superconducting solenoid magnet that is capable of approximately 19T and having specifications including Homogeneity: +/−0.01% over 10 mm on axis; Inductance: 125 Henries nominal; Operating Current: 105 amperes (17T, 4.2K); Clear Bore: 52 mm diameter; Overall Length: 385 mm (including low-field region coils); and Outside Diameter: 279 mm is described at the web page http://www.cryomagnetics.com/17-19t.htm. Other types of magnets and the fields they can attain include resistive DC magnets (~35 T), hybrid DC magnets (resistive+superconducting) (~45 T), 'long-pulse' magnets (100 ms) (~60 T), 'short-pulse' magnets (few ms) (~100 T) and explosive short-pulse magnets (~2,800 T), that are made from non-magnetic materials such as beryllium and titanium that are available from Gatan Inc., 5933 Coronado Lane, Pleasanton, Calif., USA.

We should use such machine to generate and apply strong magnetic field that will dominantly orientate or re-magnetize tiny magnets in the softened areas of microspheres or heat that area to the magnetization temperature or above the Curie temperature of the tiny magnets we are using.

Methods:

1. Aim #1 will be done in the 1st-3rd months. While purchasing, the vendor will show their laser-machine can soften 2,000 nm into a solid plastic containing dyes, possibly in mini seconds, under a microscope. The vendor should further suggest parameter-settings of their laser-machine, for our following steps. We may also do computer simulations. We already know well enough about all the parameters, including laser-wavelength, pulse-duration, energy-setting, heating-time, interval-time, laser-dye and concentrations.

2. Aim #2 will be done in the 4th-5th months. Determine the parameter-settings for softening a whole microsphere, We will use the ($1^{st}$-microspheres (Materials 2a), in oil suspension, at −20 or 0° C., and without swirling during the heating-time and interval-time. We will (1) apply a magnetic field to pull all the microspheres to the top-surface of the suspension, (2) apply pulsed laser beam with the suggested parameter-settings to the suspension, with a interval-time of 10 seconds then a brief-swirling following each heating, (3) get sample from the top surface, and analyze, (4) repeat (1)-(3) with changes to only one parameter until we find the best setting, such as to the energy-setting until we find the lowest energy-setting that cause all the tiny magnets to align at one side of some microspheres, when viewed under a fluorescent-microscope. Then find the shortest interval-time.

3. Aim #3 will be done in the 6th-8th months. Determine parameter-settings for softening 200 nm into the microsphere. We will do the same as step 2, but keep shortening the heating-time or puke-duration, and possibly increasing the energy-setting, until we see, under a fluorescent-microscope, about 200 nm deep into some microspheres contains the aligned tiny magnets. Just in case we run out of time for this step, yet, the laser-machine still softens more than 400 nm, we will, from this step on, switch to the 500,000 nm spheres. We will soften 400 nm or more into the bigger spheres that contain tiny magnets in the softened layer.

In this step, we will also determine a final concentration of the IR-dyes in the microspheres, by separately testing each of the five concentrations (Materials #2). The 0% concentration might work too, because the tiny magnets might absorb the laser and pass the heat to the surrounding polypropylene.

Figure 12:
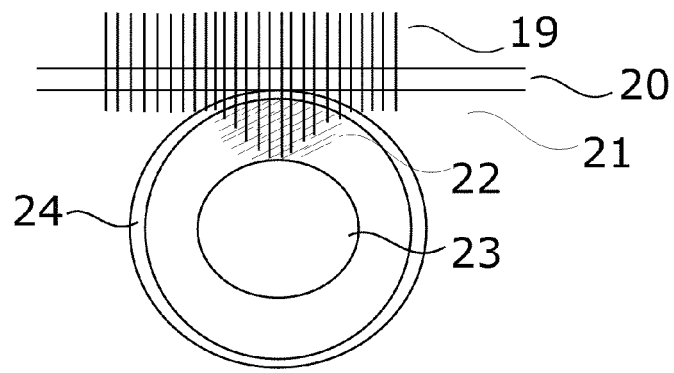
FIG. 12 shows a cross-section view of using laser to heat the top-area of a microsphere to the magnetization temperature or above the Curie temperature or to soften the polypropylene in the top-area.

Optionally, we may add IR-dyes into the oil. We will determine the concentration of the dyes in the oil. The concentration may be saturating, or higher than that in the microspheres. As shown in FIG. 12, the IR-dyes in the oil will not affect FR-irradiation to the top-area, but may block or detenuate some IR-irradiation to other areas of a microsphere, which helps to soften the desired top-area in a microsphere. This is only optional. We may not need IR-dyes in the oil at all.

In FIG. 12, a microsphere contains a hard core, '23', a shell of tiny-magnets copolymerized with thermoplastic, and an outmost layer of a glass-shell, '24'. The microsphere is suspended in oil, '21', which may contain IR-dyes. The top of the oil is covered with a piece of glass, '20', that allows IR-laser, '19', to pass through to irradiate the microsphere, so to soften the top-area, '22', of the microsphere, or to heat magnetic materials in the top-area to the magnetization temperature or above the Curie temperature.

4. Aim #4 will be done in the 9th-10th months. Determine the speed to swirl the suspension. While applying magnetic field to the swirling-suspension, we will apply laser-beam with parameter-settings determined in step 3, keep doing this while lowering the swirling-speed until we see, under a fluorescent-microscope, about 200 nm deep into some microspheres contains the aligned tiny magnets. Swirling continuously in the fastest working speed will keep the top layer of the suspension cold, so to narrow the 200-nm-deep-softened-top-area. If such continuous-swirling causes problems, we may use the brief-swirling as in step 2.

From this step on, we will use the $2^{nd}$-microspheres (Materials 2b) that contain hard-cores (FIG. 2). The hard-core will help heat the top-area bottom-up, block the IR-beam from passing through, prevent the tiny magnets from getting into the center, and cool down the softened area after each heating. We need the hard-core now. We may remove it to make room for more tiny magnets in Phase II.

We may add a piece of glass to the top of the suspension (FIG. 12), to prevent microspheres from getting out, and to help cool down the softened areas after each heating. The glass should allow the laser to pass through freely. We may further add a fen to blow cold air on to the glass, or directly to the suspension.

5. Aim #5 will be done in the 11th-16th months. We will transfer the $2^{nd}$-microspheres into UMC, using the procedure shown in FIG. 3.

In FIG. 3, a microsphere, '1', contains tiny magnets, '2'. A laser-heater, '7', heats and softens the top-area of the microsphere and, a Magnetic-Source, '5', using its S pole to orientate the tiny magnets and let them point their N poles outwards.

(5.1) The laser-heater will use parameter-settings obtained in step 3. Each heating will soften 200 nm into the top-areas of a microspheres or raise those top-areas to the magnetization temperature or above the Curie temperature of the tiny-magnets installed in the microsphere.

(5.2) The Magnetic-Source may be a Magnetic-field-generating-equipment (Materials #3). It will apply a strong, controlled, and possibly pulsed magnetic field, to magnetize or re-magnetize the heated top-area, or to polarize the softened top-area by dominantly aligning the tiny magnets in it. In case of magnetizing, the Magnetic-Source should be so strong that it will magnetize the tiny magnets to their maximum strength regardless of the magnetic condition in or around each of those tiny magnets.

(5.3) The microsphere-oil-suspension will stay cold, possibly at −20° C., so to quickly cool down the softened top-areas, to fix the aligned tiny magnets or the magnetism in those top-areas, during the interval-time.

The above (5.1)-(5.3) will repeat over and over again, because we will spin the microspheres and move them up and down, either by continuous-swirling with the speed obtained in step 4 or brief-swirling as in step 2. Over times, enough numbers of the tiny magnets will get aligned and fixed in some microspheres, or most top-areas of some microspheres get magnetized or re-magnetized. Each of them gets enough area of unipolar magnetic exterior surfaces, enough exterior surface magnetic unipolarity, or a dominating magnetic polarity around its exterior surface so that they can be pushed around by a magnet. We call such pushable micro particles UMC and thus we get the UMC.

The container of the suspension may be a kitchen-blender made of non-magnetic materials, with the blade-edges being sanded off. The blender is plugged into a potential-meter for controlling the stirring-speed. The blades will swirl the oil suspension inside the blender. We may also use ultrasound or any other means to stir the solution for keeping the microspheres spin and move up and down. The blender will sit in ice-cold-water to stay at 0° C. or in dry-ice to stay at −20° C.

Every few hours, we will stop the process, and then apply another magnetic-field to push the finished UMC to the further side of the container for collection, and pull the unfinished microspheres closer, for further processing.

The SiO2 coating around the microsphere allows the laser beam to go through freely. It will stay hard when the polypropylene below it is softened. It will keep the magnets inside the microsphere.

In case we use UV-unstable-IR-dyes in the microspheres, we may simultaneously, or a little bit lately, apply UV when we apply the laser-heating. The UV will decompose the IR-dyes in the exposed and finished-areas, so that the finished-areas will stay hard upon further laser exposures.

Optionally, we will add a second bulk-magnet to the container. This magnet, if added at the top, will push the finished UMC to the bottom, or push the finished areas of a microsphere to the lower side, for less laser-exposure; while pulling unfinished microspheres to the top, or pulling unfinished areas of a microsphere to the top-side, for more laser exposures. If this magnet is added to the side of the container, it will constantly push away the finished UMC to the further side to where we do not apply the laser; while pulling the unfinished microspheres to the closer side for laser exposures. This second magnetic field should be weak, so that the swirling will dominate the movements of the microspheres. This second magnetic field should also be applied in proper times.

In this step, we will adjust many parameter-settings based on steps 3-4 and may even repeat steps 3-4, back and forth.

6. Aim #6 will be done in the 17th-18th months. We will use a magnet to push the UMC to a layer of clean oil, concentrate them, put the concentrated sample under a microscope, and push the UMC in the sample with magnetic repulsion. We will take pictures and video-tape the pushing process, so to demonstrate the UMC are feasible for 3D-tumor-targeting. Our phase I will successfully complete here.

With naked eyes, we cannot see the UMC individually, but we can see a swamp or a locus of them when they come together, especially when they are fluorescently marked. if we prepare enough UMC, we will concentrate the UMC as a locus, then push the locus to different targets, mimicking the 3D-tumor-targeting, and video-tape this process. This will be a super plus to our Phase I.

Q&A:

(1) Will this research work?

It is pioneering to prepare the UMC, however, all the technologies needed are already there. Current technologies in laser and computer can offer much more than we need for the UMC preparation. The PRK-Laser can remove 0.25-nm-deep and 0.25-um-wide of tissues into the corneal of our eyes (http://prk.com), without collateral damages to the deeper and surrounding tissues, The printing, DVD-digital-data-storage, and pulsed-laser-engraving and welding also offer advanced laser technologies (B. Peter, et al). All we have to do is to buy a laser-machine and find the right pulse-duration, heating-time, and energy-parameters, with the help of computer-simulation and experiments.

Current technologies allow us to prepare as small as 100-nm-sized UMC. However, in this Phase I, we propose to prepare as big as 2,000-nm-sized UMC.

The proposed UMC might already work for liver-cancers because the UMC can be pushed around freely through the hepatic sinusoids that are 2-8 microns in width.

Additionally, we have an option to increase the size of the microspheres. Spheres of 800,000 nm in size are being used for tumor-magnetic-targeting and 1,200,000 nm are being used for targeted-embolization.

The key is to make good use of the current-technologies that are incorporated into a laser-machine. We will work closely with the vendor. We may prepare UMC in nano scales. We may use any other laser-wavelengths in this process or specific stages of this process. We may use a combination of laser-wavelengths.

(2) In steps 2-3, the microspheres come to the top surface?

The microspheres do not have magnetic moment due to the tiny magnets in them are disorientated. However, when we apply very strong magnetic field from the top, they will come to the top-surface.

An alternative is to heat the suspension to 160° C., apply N polar magnetic field to the suspension, cool down the suspension, and then, start steps 2 or 3 using S polar magnetic field, Identifying the right orientation by the shape of the tiny magnets.

Isolation, Grading, and Purification

The following method, when applicable, also applies to the isolation, grading, and purification of SMC (Superconductor Medicine Carrier).

Here we come to the first embodiment of isolating the UMC (Unipolar Medicine Carriers). After the preparation, we will add another step to isolate the UMC from dipolar magnetic particles, by applying same polar external magnetic forces. For example, we may apply a magnetic force to the medium or container that contains the particles either constantly or in pulsating. The magnetic force should be the same polar to the surface pole of the UMC. The force will attract all dipole particles or tiny magnets to it and repel the UMC to the other end. We may then collect the medium at the other end to harvest the UMC. Such as if the medium is water, we collect the water at the other end of the container. If the magnetic force comes from the bottom, we collect the water at the top. If we add a layer of another solvent at the top or bottom and then apply the force from the opposite end of the medium, the force will repel the UMC into the new layer. For isolating PMC, such as those contains diamagnetic materials, we may apply magnetic force to the container containing the PMC and collect the PMC at the further end of the container, in a similar we as we isolate the UMC.

Here is the second embodiment of isolating the UMC. In order to isolate top quality unipolar particles, we may add the solution, air, or other medium that suspends the particles into a tube and allow the medium to flow, in the mean time, we apply a same polar magnetic force against the flow direction. Good UMC will be stopped or even go backward against the flow due to the repelling force from the external magnet but poor UMC will go along with the flow slowly and dipolar ones will go faster than the flow. Best grade UMC will flow slowest, medium grade UMC will flow faster, so on, and worst grade UMC will flow fastest. In the tube, we may add separators that may be similar to the valves for tap water. The separators or valves may be manually or electronically operated to turn the tube on or shut it off. Once different grade UMC are separated, we may shut off the tube then collect the different grade UMC from different fractions. By collecting different fractions of the solution, we isolate and purify the UMC in different grade in terms of their uni-polarities and strength of unipolar magnetism. Or we move the magnetic source from one end of the tube toward the other end to push UMC away, possibly to another layer or out of the tube for collection, when the medium is flowing or not flowing. We may separate different grades by increasing the speed of the flowing so that poor grade UMC will be flowed out of the tube at slow flowing speed and better grades will come out when the flow speeds in faster. Further more, we may also use other chromatography methods, combined with external magnetic fields, for the grading of the UMC. PMC may be graded in the same way other than we do not need to specify the polarity of the external magnetic force.

Here is the third embodiment of isolating the UMC. The size and magnetism of the UMC can be further isolated or separated by centrifugation or ultracentrifugation, with or without against a same polar magnetic field. We may also use gel-electrophoresis, such as poly-acrylamide gel-electrophoresis with or without SDS to separate different sized particles.

The applied magnetic pushing fields may come from bulk magnets, bulk super-conductive magnets, superconductive Meissner effect, Superconductive suspension effect, electromagnets, or just electric current flowing in the wires that are wrapped around the container or the tube described above.

Here we come to the embodiment of purifying the UMC. After the UMC are collected along with the medium, we may further isolate the particles from the medium by attracting them to a magnet with the opposite pole. Such as if the medium is water, we collect the water containing the UMC, and then use a magnet to attract the UMC out of the water to a membrane, with the opposite pole to the surface pole of the UMC.

3D-Tumor-Targeting

The following descriptions, whenever applicable, also apply to SMC (Superconducting Medicine Carriers).

Now we come to the first embodiment to do 3D-tumor-targeting. Once a swamp of UMC is administered into a patient, we may use external magnetic force to push the swamp. The polarity of the applied magnetic force should like the dominating polarity of the exterior surface of the UMC. In case of SMC, the polarity of the applied magnetic source is not important. We may apply same polar magnetic forces stereo from all directions, such as from four directions, each are geometrically located in the space. The magnetic sources are positioned stereo-symmetrically to apply the external magnetic forces in a way that the swamp receives the force of same polar magnetic forces from all directions. It is obvious that, with proper adjustment the magnetic strength or the magnetic gradient will thus create a center or focus. All external magnets may face their north pole to a swamp.

If we use only one external magnet to push the swamp for the 3D-targeting, we may move the magnet around the swamp of UMC to apply the magnetic force from different directions. We may push around the swamp by putting the magnet closer to the swamp at a location or further away at another location. We may also push around the UMC by increasing or decreasing the magnetic strength of the magnet, at specific locations, if the magnetic strength is adjustable.

We may reroute the magnetic lines by adding a good conductor, such as mul metal, at the other end of the patient for the purpose of keeping the magnetic line straight through the patient. The good conductor can be added anywhere, not just at the other end, in order to reroute the magnetic lines in desired ways.

Here is the second embodiment of the 3D-tumor-targeting. We will use super-conductors to push around dipolar-magnetic-carriers (DMC) or UMC. Once the transition from the normal state to the superconducting state occurs to a super-conductor, external magnetic fields can't penetrate the superconductor, and, therefore, the superconductor generates a magnetic repulsion that can push around a magnet. This effect is called the Meissner effect. Either DMC or UMC can be pushed around by a superconductor.

We may also use both magnets and superconductors to push the medicine-carriers in vivo, at different times in a programmatic way.

Here is the third embodiment of the 3D-tumor-targeting. We will use the super-conducting levitation in combination with the superconducting suspension for magnetic targeting. The levitation plus suspension not just push, but also attract the medicine carriers to a centered location, in specific distances from the superconductor. We can put the centered location to a desired region in vivo, such as to the center of a tumor, for focusing the medicine-carriers to the tumor. Both the pushing and pulling forces of the levitation and suspension will be used for pushing or pulling the particles to desired locations in vivo, and for concentrating them in the locations. We may first push a swamp of magnetic particles to a desire location with the magnetic-repulsion, or directly inject the swamp there such as into the center of a tumor under the guidance of such as CT and let them to expand, possibly by diffusion, then move the forces around the swamp to shape the swamp to the tumor or focus them to a defined area. The external superconductor or in vivo superconductive medicine-carriers may go through the flux trapping effect, with defined magnetic-strength.

When using the superconducting levitation or suspension, the medicine carriers are aligned, facing one common pole, say N pole, to the superconductor, and the opposite pole, say S pole, to the other side. We may use external magnetic forces, magnets, or additional superconductors that may face their opposite poles, S pole in this example, to the swamp at the other side, or near the other side, of the swamp to push the swamp closer to the superconductor; or same pole, N pole in this example, to pull the swamp further away from the superconductor, or use both pull or push forces to change the location of the swamp to help the superconductor, when necessary. All these sources may be put in stereo 3D locations, from all directions, around the swamp. The additional magnetic force(s) may also help the fluxes generated by the magnetic-carriers to reach the external superconductor(s).

In all of the embodiments, the external magnets can be replaced by electromagnetic sources, superconductive magnets and/or other objects made of diamagnetic materials) such as graphite, Bismuth, Pyrolytic graphite, even frog meat or any other things, etc. They can be used to push each other or being pushed by each other, or by external magnetic force, superconductor, or diamagnetic materials. They can also be used to push nano or micro magnets and magnetic medicine-carriers, in the way of diamagnetic levitation. The magnets, the electromagnetic sources, and or superconductors may be kept at very tow temperature using, for example, liquid Nitrogen or helium or solid CO2 if necessary. Recently, people discovered that at a temperature very near absolute zero an alloy of gold and indium was both a superconductor and a natural magnet. This kind of materials can also be used to make the medicine carriers or as the external pushing source to push the medicine carriers.

These materials, such as superconductor materials, diamagnetic materials, paramagnetic, room temperature superconducting materials, semiconductors, ceramic materials, ferromagnetic materials, or any other materials that can be repelled/pushed away by magnetic repulsion or any other forces such as ultrasound, can also be used to make nano or micro particles to be used in this invention. The magnetic repulsion may be generated by the superconducting Meissner effect and levitation (flux pinning), electromagnets, permanent magnets or any other sources and materials. We can also make the particles each with pyrolytic graphite surface to increase the pushing power. These particles, due to they can be pushed around by magnets, super conductors or diamagnetic materials as well as they can push each other, can be used as PMC (Pushable Medicine Carriers), to be pushed around, in vivo, for magnetic targeting. For example, we may use ceramic materials to make the nano or micro particles, use external magnetic forces or any other forces such as ultrasound to push them around in vivo for magnetic targeting.

Strong focusing, Maglev, Quadrupole magnet, Sextupole magnet, and/or and any other means, such as the ultrasound, may be used in this invention, and are not departing from our invention.

Here is an embodiment of how to use the strong-focusing. The strong focusing is generated by the Quadrupole magnet. The Quadrupole magnet is a device in which two magnetic north and two magnetic south poles are arranged in alternation around an axis. In a same way a Sexpole magnet involves six pole tips: three opposing magnetic north poles and three opposing magnetic south poles. They are useful in magnetic targeting because they create a magnetic field whose magnitude grows rapidly with the radial distance from its longitudinal axis, good for pushing the UMC or SMC, or for pulling DMC. In the mean time, they can focus the particles along to the longitudinal axis, making the magnetic targeting possible. We may turn the Quadrupole magnet or the Sexpole magnet around a swamp of magnetic particles, setting the longitudinal axis focus (the center or turning point) at the center of the swamp, so to concentrate and focus the swamp. When we move the focus slowly, the Quadrupole magnet will keep the swamp as a concentrated swamp, we will be able to relocate the swamp to defined tumors.

Quadrupole magnet and the Sexpole magnet are also good for isolation and purification of the UMC. When we use them for isolation, we may collect the UMC at the opposite polar site of the magnetic field, such as N unipolar particles at the S polar magnetic field end because they will be pushed to the S direction, and the dipolar medicine carriers at the same polar side of the magnetic field, along the longitudinal axis.

We may use shielding materials in the above embodiments for helping focusing the magnetic fluxes. Shielding material can be anything such as good magnetic conductors, paramagnetic, ferromagnetic, diamagnetic and/or superconductive materials, etc.

In case each of those particles does not have magnetic moment, we may induce it to have magnetic moment at desired time(s), in vivo, with external magnetic forces, and at desired time(s) use superconductors to push the induced carrier(s) to the desired location for medical targeting. The strength, position, and direction of both the external magnetic sources and the superconductors should be control, constantly monitored and varied so that the magnetic attraction and the superconductor repulsions are well used for directing the carriers to the desired location. The external magnetic forces may be oscillating or pulsed if needed. The oscillating-magnetic-field can help the particles to be pushed forward, because when there is no magnetic field, the particles will lose magnetic moments and separate from each other due to the diffusion, once the magnetic filed is there, they regain the magnetic moments and get pushed forward a little bit by the pushing system, repeating this process will help the moving forward.

EXPERIMENT

We may do the 3D-tumor-targeting using DMC (Dipolar Medicine Carrier) with the following Experiment, which whenever applicable, also apply to UMC (Unipolar Medicine Carrier) and SMC (Superconducting Medicine Carriers).

Phase I: Use the Meissner Effect to push and concentrate nano-magnets into a swamp, move the swamp around, and shape it to targets, in oil and biospecimens.

Coming out of this research wilt be procedures for manually conducting 3D-tumor-targetings, as well as instruments for automatic operations. The instruments can even focus nanomagnets into micrsoscale tumors for microsurgeries, opening the door for therapies to cure cancers.

a. Significance and Opportunity

We propose 3D (three dimensional) tumor targeting with magnetic repulsion, based on magnets are always repelled by a superconductor due to the Meissner Effect. You can concentrate and maintain the nanomagnets as a locus, relocate and shape the locus to tumors, even focus the locus into microscale tumors.

In Phase II, we will develop procedures for manually conducting the 3D-tumor-targetings, and a 3D targeting machine for automatic operations. The machine may employ multiple superconductors, electromagnetic solenoids and magnets, each individually controlled by a computer. It utilizes the magnetic repulsion, combined with magnetic-attraction, for 3D tumor targeting and concentrations.

This research enables nanomagnets multifunctional. (1) It will open the door for many therapies to clear up tumors. (2) It will also enable fluoroscopy, ultrasound, and MRI to identify microscale tumors and quantities their masses, by bringing higher concentration contrast agents to tumors.

b. Experiment Technical Objectives

Aims:

1. Establish a working-system, in the first six months.

(1.1). Find out the best sized nanomagnets among commercially available ones.

(1.1.a) Sizes include 25 nm, 50 nm, 75 nm, 100 nm, etc.

(1.1.b) Nanomagnets made of alloy metallic Fe, Co, Ni, Cu, Neodymium, etc.

(1.2). Find out the best-model-to-push:

Use magnetized superconductor(s); Use Meissner-Effect alone; Use Meissner Effect with flux pinning; or the above a, b, or c with the help of external magnetic fields.

(1.3). Determine the pushing-gap (the distance between the back edge of the nanomagnet-locus and the front surface of a superconductor).

2. Test in oil (or glycerol if nanomagnets are hydrophilic), 7th-8th months.

(2.1) Can we concentrate nanomagnets as a confined locus then cause the locus to move to different target locations.

(2.2) How strongly we can hold the locus in a target. (For handling blood flow)

Can we shape the locus. (For handling tumor shapes)

3. Test in biospecimens (rat brain and/or liver), 9th-11th months (3.1) Can we maintain the nanomagnets as a confined locus in a phantom, and cause this locus to move to a different target location.

(3.2) Can we hold the locus at a target as long as needed?

(3,3) Can we denature the target by heating the nanomagnet-locus with externally applied IR energy [A. Apollo, et al], while maintaining the adjacent tissues intact?

(3.4) Can we retrieve the nanomagnets after a treatment?

We believe, once accomplished, the above aims will complete the feasibility demonstration of the technology necessary to support early in-vivo testing and significantly reduce overall technical risks to the program.

c. Experiment Work Plan

Materials:

1. HTS (High Temperature Superconductor) materials, YBa2Cu3Ox (YBCO), made by Top-Seeding and Melt-Texturing (TSMT) method, GdBaCuO and GdBaCu bulk superconductor materials will be purchased from MTI Corporation located in Richmond, Calif., USA. At about $800-$2,000.

The TSMT method enables the growth of very large single-grained YBCO sample up to several centimeters in diameter and thickness. These single-grained YBCO samples consist of no weak link and the whole sample can be treated as a quasi-single crystal. In addition, the pinning strength of fluxoid can be enhanced by introducing second phase precipitation, such as Y211 particles. Each sample is capable of levitating over kilograms of weight, which is at least 3 orders of magnitude higher than that of a sintered same sized YBCO sample.

LTS materials may be bulk lead that we already have. We may also use other materials like NbTi, from Bruker Advanced Supercon, Inc., Billerica, Mass., USA.

2. To generate the superconductors, we will put bulk superconductor into a foam container, add liquid nitrogen, and wait until the Tc temperature is reached. The foam container wilt have a thin wall facing the application side.

In case we need to make low temperature superconductor, we will put the container that contains liquid Helium into another container that contains liquid Nitrogen in order to save the liquid Helium.

3. Magnetization will be performed by the pulse magnetization method (PFM) that can be done with copper wire [X., I. Huang, et al]. The bulk superconductor can generate a strong magnetic field in an open space. To generate the superconducting flux pinning, we may allow the superconductor to go through the flux trapping effect with defined strength of magnet or magnetic field, by electricity current to copper or Bismuth wires that wraps the superconductor, or simply put a bulk magnet closer to the bulk superconductor for 20 seconds.

4. Permanent Nanomagnets: TurboBeads, carboxyl, are highly magnetic nanoparticles with diameters of below 50 nm. The surface of the particles is covalently functionalized with carboxyl groups (>0.1 mmol/g). Will be purchased from: TurboBeads Llc. CH-8093 Zurich.

All other permanent nanomagnets, with specific sizes, coated with PEG (Polyethylene Glycol) and negatively charged groups, with or without gold coating, will be purchased from United Nuclear Scientific, Sandia Park, N.M. 87047, USA.

An Ultrasound Image System for real time visualization of nanomagnets as a locus on the move. The Ultrasound System (refurnished) is GE Voluson 730 BT03 EXPERT, can do Real-time 4D, Real Time 3D Imaging, 3D, Colorflow PW Doppler, All Digital Windows Based Platform, Tissue Harmonic Imaging.

The Seller is National Ultrasound Imaging Ultrasound Affordable, Georgia, USA.

Experiment Methods:

We will visualize the nanomagnet-locus on the move real time, in oil with fluorescent marks, or in biospecimens with an ultrasound-imaging-system.

1. Aim #1 will be done in the first 6 months begins on Jun. 1, 2009, and in oil dispersion.

(1.1) In the first 3 months: To determine what sized nanomagnets can be pushed around by superconductors, we will add oil into a beaker, add one kind of purchased nanomagnets that have specific sizes to the beaker, mix them by a brief stirring, then apply the superconductor to the mixture from outside the beaker to see if the nanomagnets can be pushed to the other side. Sizes will be tested are 50 nm, 75 nm, 100 nm, etc. For each test, we will use one to two drops of the commercial samples, just enough for us to see them as a locus due to their fluorescent. In this test, the pushing-gap can be as short as 35 mm, the superconductor will be a HIS cooled in liquid nitrogen with ZFC (Zero-Field-cooling) without the flux pinning.

Regarding how to make the HTS, please see our Materials #3.

Regarding how to cope with the thermal excitations, please see our Q&A #4.

(1.2) In the second 3 months: To establish the-best-model-to-push, we will push the sized nanomagnets, in the forms of ferro-nanomagnets, para-nanomagnets, Fe3O4, or etc., in oil dispersions with: (a) magnetized superconductor(s), (b) Meissner-Effect alone, using 35 mm as the pushing gap and do the ZFC (Zero-Field-cooling), (c) Meissner Effect with flux pinning, using 5 mm as the pushing gap and do FC (Field-Cooling), (d) the above a, b, or c with the help of external magnetic fields. An external magnetic field may be applied from many directions. It will help quench the thermal excitation of the nanomagnets. It might also increase the superconducting levitation force (pushing force) by increasing the induced current at the surface of the superconductor.

In the sixth month (partly): To determine the pushing-gap, we will use a. bigger container, push the nanomagnets, measure the distances, and record the results, in the same way as described above.

2. Aim #2 will he done in the 7th-8th months, and in oil dispersion.

(2.1) Seventh month: To test whether we can concentrate nanomagnets as a locus, we (a) may move a superconductor all around the beaker, include the top and the bottom, trying to point to a focus and keeping a same distance to the focus, to push and concentrate the nanomagnets to the focused region. The speed of moving the super-conductor is dependent on the diffusion speed, and we need to visualize the nanomanet-swamp to adjust the speed, using fluorescent dyes or an ultrasound system. The oil should be sticky enough to keep the diffusion slow. We may cool the oil to gain the stickiness. (b) use three superconductors, the first one being put at the top, the second one being put at the side that is 90 degrees to the first one, and the third one is 90 degrees to the first and to the second one. Then turn such structured super-conductors around the beaker, trying to point all three superconductors to a same focus and keeping them same gaps to the focus, to concentrate the nanomagnets. (c) Use six superconductors, similar to the six coil superconductor MRI machine, but face to face at the top-bottom, left-right, front-back, to concentrate the nanomagnets.

All the above experiment may be done by moving the beaker, while keeping the superconductor(s) at a fixed position. We may also combine the movement of both the superconductor(s) and the beaker.

(2.2) Eighth months (partly): To move the concentrated locus around, we may do the same as above with superconductor(s) but with sequentially changing superconductor-locations to keep the locus intact and slowly move it forward. We may slowly move forward to the beaker the superconductors that get into the position to push forward the locus, while keeping those that get into the side positions the same gaps to the locus.

To see we can hold the locus to the target, we may again do the same, but keep the superconductors a fixed gap to the locus.

To see how strongly we can hold the locus, we will gently stir the oil while maintaining the locus in the target; see how fast we can stir, (2.3) Eighth month (partly): To see we can shape the locus in oil, we may change the gaps between the locus and the differently positioned superconductors, for example, if we want to make a ball-like locus, we may keep the gaps at different positions all the same.

3. Aim #3 will be done in the 9th-11th months, and in rat brain or liver.

We will select an organ based on the sized nanomagnets. If the nanomagnets are small, around 75 nm, we wilt test them in rat brain. However, if the nanomagnets have to be bigger, we will test them in rat livers. Hepatic sinusoids are 2-8 microns in sizes. Charles River Laboratories in Wilmington, Mass. will prepare the organs fresh, and keep them at 4° C., just at the time when we are ready to pick them up. We will pick up the organs immediately. We will get back to our laboratory within 30 minutes and start the experiments immediately.

To test whether we can maintain/concentrate nanomagnets in an organ as a locus, we will inject 25 ul of nanomagnets oil dispersion to a specific area, such as under the membrane, then use the methods work in the oil-dispersion experiments to push, namely, we (1) may turn a superconductor all around the organ, include top and bottom, to push and concentrate the nanomagnets to a designed region. (2) use three superconductors, the first one being put at the top, the second one being put at the side that is 90 degrees to the first one, and the third one is 90 degrees to the first and the second one. Then move such structured superconductors around the organ to concentrate the nanomagnets. (3) Use six superconductors, similar to the six coil superconductor MRI machine, but face to face at the top-bottom, left-right, front-back, to concentrate the nanomagnets. (1) and (2) is more feasible for future in-vivo applications because the nanomagnets diffusion in the tissue is very slowly.

To move the concentrated locus, we may do the same as above with superconductor(s) at defined locations around the organ, referring method in oil tests.

To see we can hold the locus to the target, we may again do the same, for as long as we want, such as for 30 minutes, using the method similar to the oil experiments.

To see we can retrieve the nanomagnets, we may guide the locus to a superficial area, concentrate if further, then inject oil into that area and withdraw the oil, repeat a few times. We may also cut off the superficial area that contains the locus to retrieve it. We will count the ratio retrieved.

A good ultrasound imaging system will allow us to visualize the nanomagnet-locus in real time. However, to get more detailed data, we may freeze the organ, slice the organ into pieces and locate the fluorescent marked nanomagnets. We may also try the real-time in-vivo detection method as published [S. I. Takeda, et al].

To denature the targets, in the 11th months, based on the above experiments we will heat the nanomagnet-locus with externally applied IR energy which can penetrate tissues and heat only the nanomagnet [Appolo A., et al]. The nanomagnets will be coated with gold, and are commercially available from many companies. The light will be applied for 5 minutes or so. The near infrared light gives this procedure an advantage because this range (700-900 nm) is not significantly absorbed by chromopores in human tissue and can therefore penetrate more deeply [D. P. O'Neal, et al; L. P. Hirsch; et al], and within 1-2 minutes, the temperature of targeted region may rise to around 55° C. for denaturing the tissue. After the denaturing, we may slice the organ into pieces and locate the denatured tissue.

Experiment Q&A

1. Will it work? (1) The Japanese can levitate a train 100-150 mm, using EDS (electrodynamic suspension) based on the Meissner effect of LTS (low temperature superconductor). (2) The Chinese can levitate a train 20-30 mm using the Meissner effect of HTS (high Temperature Superconductor). (3) Levitation force between a permanent-magnet and a HTS-YBCO-bulk was 19.6 N at a levitation-gap of 50 mm [B. P. Martins]. (4) Levitation force between a permanent-magnet and a HTS-YBCO-bulk overcame the weight of a bulk at a 60 mm gap [G. D'Ovidio et al], (5) Levitation force was significant at 70 mm gap [H. M. Al-Khateeb, et al]. (6) Levitation force remained about the same while varying the thickness of permanent-magnets, when the gap is far. [M. K. Alqadi, et al.]. We may consider our nanomagnet-locus as a very thin layer of magnet; it will still get the same amount of push-force as that of a thick magnet, in 50-80 mm gaps.

We want to push nanomagnets that are lagged behind or at the rear edge of a nanomagnet-locus. Nanomagnets are easier to push because they may be single domain magnets and they may construct diversified-geometric-arrangements.

Most importantly, we don't need strong levitation/pushing forces. We want to use weak forces to change the course of the diffusion. Small nanoparticles can diffuse freely in tight tissues; and bigger ones in more porous tissues [Appolo A., et al]. We want to use weak forces to push nanomagnets around through interstitial spaces, or the sinusoids if in the liver, without damaging the tissues and cells.

Conclusion: We can push around nanomagnets within a 50-70 mm range, which is good enough for most clinical applications. (2) We can satisfy all clinical applications by dramatically extend the pushing-range, using LTS or external magnetic fields.

2. How do you change the strength of the levitation force (pushing force)?

The magnetic flux density of each nanomagnet is the first parameter to change. We will also add external magnetic fields to increase the pushing force. A magnetic field may be applied at the other side of the nanomagnet-locus, opposite to the superconductor. We will also try applying the magnetic field(s) in other ways, We may also lower the temperature by using liquid Helium if necessary. There are many other ways to change the levitation forces. We can change the levitation force dramatically (Yang W, et al.) by altering the thickness of the superconductors, grain-orientations, temperatures and magnetic field distributions, gaps between superconductor and the nanomagnet, etc. Levitation force F between the permanent magnet and the superconductor can be described as: $F=JJ_sx B dV$, where $J_s$ is the superconducting critical current density, B is the magnetic flux density of permanent magnet, and V is the volume of the superconducting current can flow persistently without the blockade of grain boundary weak link. Clearly, a stronger levitation force will be obtained by enhancing Jc, external magnetic flux density B, and the volume of the superconductor. TSMT samples should be used in our research because the volume is large [I. G. Chen, et al.].

3. Do geometrical-arrangements of the nanomagnets matter?

At a giving time, in-vivo nanomagnets are in many different geometrical arrangements, some can be in the perfect symmetry as described for levitations of small magnet [N. D. Valle] and others may be just OK. Because their geometrical arrangements are constantly changing, due to their thermal excitations, we should have no problem to push the nanomagnet-locus around. Also because the pushing forces are stronger to the rear nanomagnets and weaker to the front ones, nanomagnets will be concentrated in the way we want, However, if we find it is necessary to have the nanomagnets aligned in some degrees, we may quench the thermal excitations.

4. How do you overcome the thermal excitation?

Nanomagnets so small have thermal excitations like the Brownian Motion, which is what we want to prevent them from aggregate. However, we can quench the thermal excitations. (1) We may use nanomagnets made of Neodymium, neodymium-iron-boron, or any other strong magnetic materials, to quench most of the thermal excitations, (2) Use external magnetic field to quench the thermal excitation. In the real world, we will put a magnet at the other side of the body to pull the nanomagnets, while using superconductors to push them, which means we may apply magnetic field(s) to quench the thermal excitation. (3) We can change the size of the nanomagnets. Preferably the size matches the magnetic strength in such a way that when no superconductors are around, the nanomagnets do not show magnetic. When there is a superconductor around, the thermal excitement goes away and the nanomagnets get pushed around.

Superconducting-magnets and the superconducting-flux-pinning can be very strong to quench all thermal excitations without any external help. The Meissner effect alone, on the other hand, may need the help.

5. Will the nanomagnets aggregate in the tissue?

When the thermal excitation is weak, the nanomagnets start to align to form lines then the lines will aggregate. This might help the concentrating. But when the aggregates get bigger, problems arise. (1) We can do the targeting intermittently, give time for the nanomagnets to regain the thermal excitations and allow the aggregate to dissociate. (2) Keep changing navigating directions to break the lines. (3) Use pulsated levitation. (4) Chang polarities of the flux pinning or the superconducting-magnet, which means we will apply the levitation once with a flux pinning that generating N magnetic-attraction and another time with a different flux pinning that generating S magnetic-attraction, to actively dissociate the aggregate. This is achievable by alternating the current direction back and forth in the wires that surrounding the superconductor. (5) Change the polarity of the externally applied magnetic field, by keeping switching N or S polarities that is pointing to the targeting site of a magnet.

We should easily address other challenges, such as nanomagnets may get into the blood vessels due to the enhanced permeability, may cause similarities to heart attacks and strokes, have to evade the RES especially the Kupffer cells in the liver, have to limiting uptakes by normal cells, and deal with biocompatibilities.

e. Experiment Relationship with Future R&D

1. Anticipated results: (1) A sized-Nanomagnets, possibly the Turbobeads, can be pushed around by superconductor(s). (2) The-best-model-to-push is to use magnetized superconductor(s), the superconducting-Meissner-Effect with or without flux pinning, or with or without the help of external magnetic fields. (3) The pushing-gap is 50-70 mm. (4) We can concentrate nanomagnets as a locus, relocate the locus to different targets locations, and shape the locus, in oil and in animal organs. (5) We may see denatured target tissue, without damaging the adjacent tissues, by heating the nanomagnets with IR.

2. Significance for the Phase II R/R&D Effort:

In Phase II, we will test with live animal in-vivo, create protocols for Doctors to manually do the 3D tumor targeting, and manufacture our '3D Targeting Machine' for automatic operations. Other than the feasibility demonstration, results obtained in Phase I will be very useful for phase II. (1) We will use the sized-nanomagnets and the-best-model-to-push in Phase II. (2) We may switch to low temperature superconductor(s) in Phase II if we find the pushing gap is less than 75 mm. (3) Data obtained in the biospecimen test will be used in Phase II for live animal tests. The data will also help us design our '3D Targeting Machine'. (4) We will use all methods, such as the one to denature target and the one to quench the thermal excitation, work in Phase I for Phase II.

3D-Targeting Machine

Now we come to the first embodiment of our 3D-targeting-machine. Our machine applies same polar magnetic forces stereo from all directions. For example, our machine have special structure(s) allowing us to apply the external magnetic forces to the swamp from four directions, each are geometrically located in the space. They are positioned stereo-symmetrically to apply the external magnetic forces in a way that the swamp receives the force of same pole magnetic forces from all directions. It is obvious that, with proper adjustment the magnetic strength, the magnetic gradient will thus create a center or focus. All external magnets face their north pole to a swamp. The machine can be similar to the six-coil superconducting system using MRI technologies that generates electromagnetic forces from all directions, with additional features such as you can control the magnetic strength, polarity and stereo-position of each individual superconductors.

Our machine can even apply same strength and same pole magnetic force to the swamp from many stereo-directions at the same time. In the process of concentrating the swamp, our machine can apply pulsed forces, at one time, the left side sources are on while the right side sources are off, at another time, the upper side sources are one and the tower side sources are off, at still another time the right side sources are one and the left side sources are off and so on very fast intermittently. In the process of moving the swamp, such as to the right, the left side sources may have the maximum strength and all other side may be weak in order just to keep the concentration or the right side source may even be off or change to the opposite pole to for attraction in order for the swamp to move fast.

Here is the second embodiment of the 3D-targeting-machine. Our machine has special structure to use a single magnet to apply the magnetic pushing forces from all directions. The structure moves a magnet around a target and applies the magnetic force at different positions. The machine may comprise a round housing allowing a patient to fit in. The interior wait of the housing may have the special structure comprising gears and grooves, and a magnet is attached to the gears and grooves so that the magnet can slide along the interior wall, around a patient, to ail positions, such as left, right, front and back, so to push and concentrate the medicine-carriers inside the patient. The machine may further have rod pointing to the center with gears to protrude the magnet closer to the center or retract back, so to push the concentrated medicine-carriers around. We may also push around the concentrated medicine-carriers by increasing or decreasing the magnetic strength of the magnet, at specific locations.

Figure 9:
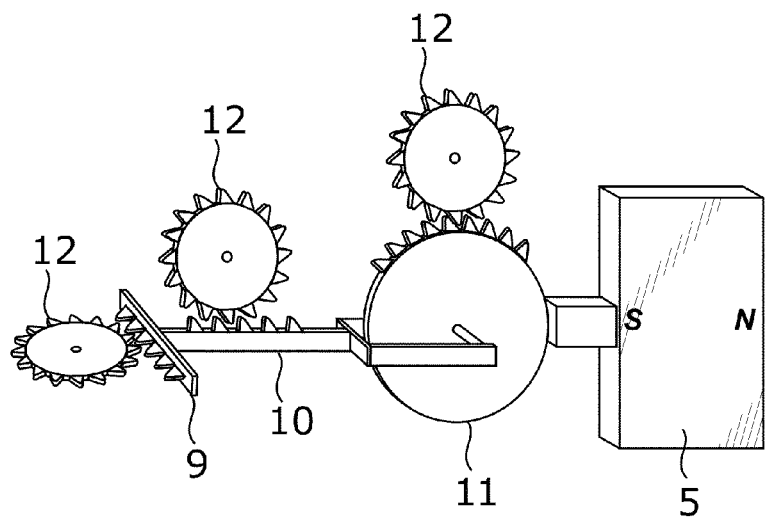
FIG. 9 shows a unit of a 'bulk pushing source'.

Our machine may be build up by a single bulk source which is shown as a whole unit in FIG. 9. The pushing/pulling magnetic source, '5', may be made of a single bulk magnet, electromagnet, superconductor, Creaky levitation, Levitron (Spin stabilized magnetic levitation and the bulk source can be a spinning magnet for pushing the medicine-carriers), solenoids, Halback arrangement (such as use the standard Halbach Arrays for standard levitations), wire circles/solenoid that can generate magnetic force when electric-current going through, superconducting magnets, or any other bulk object that can levitate and/or apply pushing and/or pull force(s) to the Medicine Carriers. The pushing/pulling source may be installed on a ball, '11', which may have zigzag teeth, the ball is placed in adjacent to gears, '12', that also has zigzag teeth fit into the teeth on the ball. The gears may turn the ball and so to turn the pushing/pulling source up and down, according to the computer control system. The unit also has a holding pole '10' that has zigzag teeth and works with another gear '12' which may protrude or retract the magnetic source so to move it closer or further from the patient, according to the computer controlling system. The unit further has a rod, '9', with zigzag and works with a gear, '12', that turn the magnetic source inside or out, to complete the three dimensional control of the magnetic pushing/pulling source. The machine can also change the strength of the source such as by changing the electric current flowing in the electromagnet or solenoids. The machine can also rotate and change the bulk source in many different ways, such as by adding more gearing systems. All these changes may be controlled by a computer and in response to the location and shape of a tumor.

To use superconductors as the bulk source, we will lower the temperature of the bulk superconducting material, and wait until the Tc temperature is reached, such as low-Tc superconducting coil at liquid helium temperature, or high-Tc superconducting coil at liquid nitrogen temperature. Zero-Field-Cooling might be used here.

To use superconducting suspension as the bulk source, we may allow the superconductor to go through the flux trapping effect with defined strength of magnet or magnetic field, or simply put a bulk magnet closer to the bulk superconductor for a few seconds.

Figure 10:
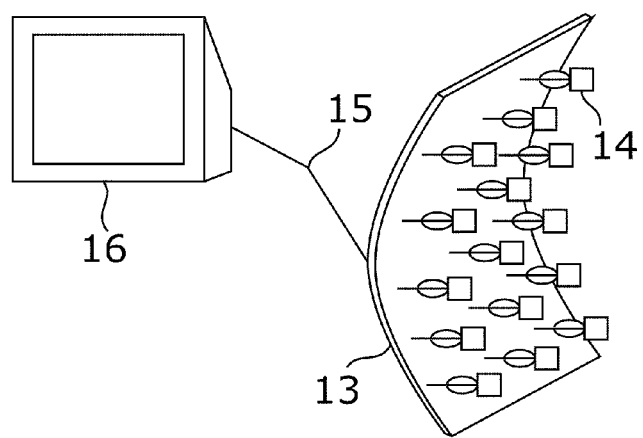
FIG. 10 shows wall like unit that contains many 'bulk pushing sources' with a computer.

In FIG. 10, we show part of our machine. The wall like unit, '13', is shaped and sized. It may be equipped with one, or even thousands of individual bulk sources, each as shown in '14', which is the whole unit as shown in FIG. 7. They may be installed in a single layer or multiple layers. The wall unit may surround a housing that is shaped and sized, such as just big enough to let the header fit in, but with a hole for the neck to protrude out. Different bulk sources may be made by different material, each is controlled by a computer individually, can protrude out or retract in, can do whatever as described above, responding to the signals send from the computer, '16', through wires '15', so that as a whole, they can relocate and concentrate the medicine-carriers to the desired location in vivo.

The computer has special software that may automatically control the size, shape, and location of the swamp of particles by sending singles to adjust the strength, position and/or direction of the external bulk pushing sources, based on the location and the shape of the medicine-carriers and the tumor(s). Our soft-wares may acquire information about the shape and position of the medicine-carriers and the tumors from ultrasound and any other imaging systems, such as fluoroscopy, CT, or magnetic imaging. The computer will send signals for push the swamp into a tumor and shape the swamp to the tumor. In case the medicine-carriers are shaped as a wall, the CT should have it focus-surface set at or in the wall fitting right into the wall, cover or overlap the wall, and move forward together with the wall.

Our 3D-targeting-machine distinguishes itself by employing the magnetic repulsion. It employs magnetic repulsions come from all different sources, such as superconducting Meissner effect and like pole magnets It pushes, pulls, navigates, concentrates, focuses and controls nano or micro particles, that are paramagnetic, ferro-magnetic, ferrimagnetic, permanent magnets, or any other kind of magnetic, to specific locations in vivo and shape the particles to the desired shapes such as to the shape of a tumor.

Figure 11:
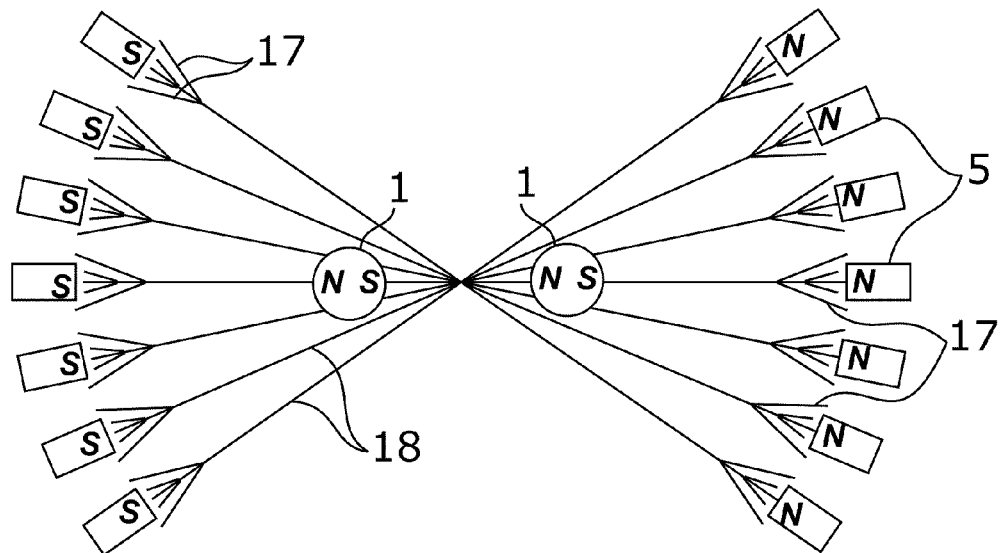
FIG. 11 is a cross-section view of an embodiment that uses the superconductor-plates to focus magnetic-fluxes from each magnet into a high beam, then, organize the magnets to focus all the beams to a center that pulls dipolar magnetic particles to it.

Here is the second embodiment of our 3D-targeting-machine, we have FIG. 11 which shows: We use superconductor plate, '17', to cover around one end of a magnet, '5', so that the flux from the magnet will be concentrated into a sharp beam, '18'. With special arrangements, such as the magnets at our right point their N poles to the center and the magnets at our left point their S poles to the center, we can focus all the beams into a center. The center gets the highest magnetic field, and the magnetic gradient goes down around it while the distances from it increases, in certain range. If a dipolar magnetic particle, '1', is placed within that range, it will be attracted to the center. If it is at our right, its N pole will be attracted to the center. if it is at our left, its S pole will be attracted to the center. All particles in that range will be attracted to the center. This is just a cross-section view, showing the two dimensions. We will, in real, do it in a three dimensional manner, like the one showing in FIG. 10 to be with superconductor plates to focus the flux of a magnet into a high beam. We can create a high magnetic center in a three dimensional way, anywhere inside the body. We can move the center to a tumor by regulating the magnets, for tumor targeting.

Clinical Applications

Now we come to the embodiment of clinical applications. As shown in FIG. 2, to destroy a tumor, '6', with radioisotopes like rhenium-188 or I-131, we may prepare tens of thousands of PMC (Pushable Medicine Carriers), '1', label the PMC with enough radioisotopes, such as 800 mci, then inject a swamp of PMC into the brain fluid either outside or inside the hard membrane. The swamp can also be administered orally, intravenously, through an artery, or into a local tissue. We may use external magnets, '5', to push the PMC into the tumor.

In case of orally administration, we want the PMC to have some hydrophobic groups or any other active-groups that facilitate the absorption by the stomach, intestines, etc. We may use the magnetic-repulsion to control the absorption at exact locations. Once absorbed, we will push the PMC to the desired location. The PMC will get into the liver, and the active-groups should allow the liver to change their properties, such as adding oxygen by cytochrome P450 to make the carriers hydrophilic, and, after the treatment, we will push them to the gull-bladder so they will get to the intestines again, but this time they will get out from the body. The PMC may also be pushed to the urine to get out. If we want to recover them from none natural routes, we may relocate them to the skin, a vein or anywhere we can use a needle to draw or a knife to cut them out.

Once recovered, we may purify, autoclave, and then reuse them. If they loose their magnetism during the autoclaving, we may let them go through the conversion process again to convert them back to UMC.

The swamp may be under the external magnetic-repulsion control during the injection. After the injection, the swamp will be brought to the control or focus of the externally applied forces, such as the stereo-magnetic forces. The external magnetic forces come from many directions, as shown in FIG. 2 four magnets in the cross-section, one in the front and the other behind is not shown.

These forces will concentrate the swamp but keep it in a big size so that the radiation will be weak not to harm the surrounding tissues. The stereo forces will then move the swamp to the tumor. During the moving, the threes against the moving may be shut off or even turned opposite so to attract the swamp, the threes that are at the sides will be kept strong, enough to keep the swamp narrow but not so narrow for the radiation to hurt the tissue, the forces that are pushing the swamp along the direction may be kept at maximum strength in order to push forward the swamp and keep the swamp short, but not so short for the radiation to hurt the tissue. All these forces or magnets may be applied in a constant, pulsated, and/or oscillated manner intermittently, or persistently.

One or more controller(s) will be in charge to turn on or off the forces, adjust the strength, and position the threes. Once the swamp gets to the target region, the controller may turn on all forces and apply forces from all directions to concentrate and reshape the swamp. In case these forces are not oppositely faces each other, such as in the case of only one force is used, the machine will spin and turn the force(s) around the swamp, to keep the swamp together and moving, focusing, and shaping the swamp to a tumor. The size of the swamp can be squeezed so small that the radiation can kill all the cells in a desired time. If for hours, we may let the particles get trapped in the tumor by using a specific size of the particles, get linked to the tissues by chemical active groups, antibodies or charges, or simple keep applying the forces to keep the particles there. As cancer cells are more sensitive to radiations, we may treat the cancerous area for a predetermined time that will ensure all cancer cells get killed but normal cells will survive any injuries. The length of the predetermined time depends on the type of cancer, the type of tissue the cancer, the location of the area and many other factors. We need experiments to determine it. Once the treatment is finished, the machine will decrease the strength of the stereo-magnetic forces so to allow the swamp to expand so to decrease the radiation strength, and then move the swamp to a location where the swamp can be easily withdrawn by a needle and syringe.

Moving the PMC (Pushable Medicine Carriers) in different tissues will need different strategies and methods. Specific methods will be developed for each organ and tissue, based on the knowledge of the tissue structure as well as results from experiments. Such as in the liver, the carriers will be moved through the hepatic sinusoids that are 2-8 microns in width, we may use 1-2 micron sized UMC. However, because of the hepatic sinusoid are very irregular, we need to slightly changing the direction of the applied external magnetic forces and even need pulsated forces to move them back and forth at certain point. In the muscle, we need to move the carriers in the direction of the muscle cells through the intercellular spaces.

The above procedure may also be used for the following treatments:

Treatment 1: We may use the same procedure as the above but replace the radiation by heating-energy. In this treatment, the particles serve as medium to absorb heating energies, the particles may contain materials that get heated easily when external energies such as microwaves, IR, or pulsed magnetic fields is applied, Laser-induced, microwave and radio-frequency induced, magnetic induced and focused ultrasound induced heat may also be used. When us IR, the wavelength should be selected. Light at wavelengths between 800 and 1200 nm can go through tissues with relatively little attenuation, and heat the particles or carriers. Once the particles are heated, they will heat the tissue. Tumor cells can be killed at 45° C. Normal cells can manage to survive such medium heating. This is hyperthermia treatment. For thermal ablation, we may heat the subject tissue to a temperature around 55° C., or even 75° C. We might use Gold sulfide nanoshells that are been incorporated into poly (NIPAAm-co-AAm) hydrogels for this purpose, Thermal ablation may cause internal bleeding due to damages to blood vessels. We may increase the temperature to higher, such as 300 degrees or even higher at the site of potential bleeding or already bleeding, to prevent or stop the bleeding.

The tissue temperature may be governed by the nature and concentration of particles in the tissue, as well as the heating time and energy applied. Experiments may be carried out in vitro, such as with water or real tissues, to know how to heat a specific tissue to a specific temperature, for in vivo real treatments.

Treatment 2: Boron neutron capture therapy is good for brain tumors. The boron(10) explosion will kill cells that are directly adjacent to it only. We may use the same procedure as the above just replace the radioisotopes with boron(10). Once the particles are concentrated into the tumor, we apply neutron beams to cause the boron(10) to explode, Treatment 3: Photodynamic therapy, when enhanced by magnetic targeting, will be a very promising cancer treatment. Photosensitizers, such as the FDA approved photopharyn, may be carried to the cancerous region by the PMC (Pushable Medicine Carriers), then administer luminescent labeled unipolar particles using similar procedures as the above. The photosensitizer(s) may be carried to the cancerous region with the carriers that carry the luminescent agents at the same time. We may also first administer the PMC that carry the luminescent agent then administer the photosensitizers or the PMC bearing the photosensitizers. We may further do it in other different sequences. The time for the particles to stay in the area is critical. If too long, all cells will be killed. If too short, only a minimum amount of cancer cells may be killed. We should move the particles out of the area and the body just in time. And we may need experiment to determine how long the particles should stay.

In a similar way, the particles can be used for targeted drug delivery. They can deliver drugs and other medicines such as enzymes, vectors, prodrugs, antibodies and chemotherapeutic agents, directly into the tumor or in close proximity of the tumor in vivo. The particles can carry a single, a pleural or all know medicines in one single trip. The particles can release the medicines in a controlled manner. Again, N-isopropylacrylamide (NIPAAm) and acrylamide (AAm) can be used for this purpose like the thermal ablation. Our 'medicine delivery' means drug, radiation, thermal delivery etc.

We may combine different treatments such as targeted hyperthermia treatment with targeted chemotherapy, etc.

During the treatment, a camera will monitor the exact location and shape of the swamp. The shape, size and location of the tumor should be welt defined before the treatment or during the treatment when monitoring the swamp.

In case there are many small tumors spread in a organ like brain and liver, we may add more external magnet sources to create multiple magnetic focuses, each control a small swamp of particles, so to have multi-microsurgeries in the above way simultaneously.

Again in case of there are many tiny tumors spread everywhere in a area of tissue or in an organ like brain and liver, We may concentrate the particles as a wall, using laser IR beams to destroy the tumors in the wall, while moving the wall forward. The wall may form in the tissue or organ and in the intercellular spaces or in blood vessels, capillaries, and/or special tissue spaces such as the hepatic sinusoids. The wall may move from one end of the organ to the other end.

If the wall is formed through blood vessels and capillaries, the blood movement may push the carriers forward. The magnetic force may push against the blood floor to keep the wall in shape. We may either maintain the wait at around 45° C. while moving it forward so to selectively kill cancer cells in its pathway, using the hyperthermia treatment. We may also use laser beams to heat tumors to 55° C. to destroy all tumors in the wall, while moving the wall forward, so to destroy all tumor in its pathway, using the thermal-ablation. The wall should move with a controlled speed so that enough heating will be applied to the tissue in the pathway. The heating energy, heating time, and concentration of the particles must be controlled in order to get the proper temperature.

We can identify a tumor in the wall and do the thermal ablation simultaneously. The carriers in the wall may also serve as good contrast agents, such as iron, for MRI to see and locate a tiny tumor in the wall, we may also use other means such as ultrasound to see and locate the tumor, and once located, we destroy it, with exactly controlled laser beam, both in terms of energy and targeting, to heat the particles in that location so to destroy the tumor in the wall. When wall can not cover a whole tumor, this method can destroy the part that is in the wall, when the wall is moving forward, we destroy the whole tumor, part by part. We may also move more particles in to the tumor from nearby regions when necessary, to increase the thickness so to cover the whole tumor.

We may further destroy multiple tumors simultaneously in that wall, using multiple targeted laser beams. For example, the wall is moving and when we see thousands of tumors in the wall, we use thousands of laser beams to destroy them, so to destroy millions of tumors in the pathway of the wall.

We may further do hyperthermia treatment with the moving wall. We may use an energy, such as IR, to maintain the wall at 42-45° C. while moving the wall forward so to selectively kill cancer cells while retain normal cell in the wall-pathway.

To block the blood supply to a tumor (Embolization), we may inject the PMC (Pushable Medicine Carriers), and then stop the PMC in selected blood vessels, preferable a small artery, by applying a strong magnetic repulsion against the blood flood. The injection may continue until enough amounts of the PMC are accumulated. in that selected blood vessels. This will block the blood supply, which is useful in the treatment of strokes, cancers, etc.

To unblock a blood vessel that is narrowed or already blocked by cholesterols, we may forcefully push the PMC through the narrowed or blocked vessel, which is useful for heart attack(s), etc.

We may also allow the tiny magnets that makes up the UMC (Unipolar Medicine Carriers) to dissociate, which can be achieved in many ways such as using enzyme to cut off the linking polymer, or let the water to dissolve the material that hold the tiny magnets. Once the tiny magnets are dissociated from the UMC, they will aggregate and stay where they are, which is useful for keeping drugs in the desired location, keeping the blood supply blocked, etc.

A swamp of PMC may also be injected directly to a desired location, such as to the center of a tumor, with a long needle, under CT or three dimensional MRI, ultrasounds, or any other means.

This invention may also have the following potentials. (1) The PMC can get to anywhere in vivo: As magnetic forces can even lift a million pound train, the external magnetic forces we use can be so strong that they may force the particles to go against the blood flow in the artery and veins, penetrate the vein valves, and penetrate the blood vessels, tissues, organs and organ membranes. (2) The external forces can squeeze the PMC to a extreme density at the center of a tumor then suddenly loose the forces to let the PMC fly and expand outward at a speed to cause the cell to die, therefore, destroy the tumor when this process is repeated. (3) When the forces is increased further, the PMC will be in contact with each other, the tiny magnets of one PMC may get inserted into the other PMC which will in turn cause the PMC to aggregate together, so all of them will stay to that particular location forever. (4) The forces may be applied intermittently from different directions. The particles can release polar components at the diseased area and the polar components can be made to spin due to external forces. The spinning can kill cancer cells. (5) As the magnetic forces can be very strong, the machine can also push and place some other devices, such as a blood vessel support means, to the heart, the brain and other organs if the device is unipolar at its surface. (6) Target multiple cancers or even more broadly for target multiple diseases.

In addition to the above, the particles will be useful for:
Early detection of diseases including atherosclerosis (thickening of arterial walls,) thrombosis (formation of clots) and heart attacks;
Understand metastasis of tumors (Metastasis is the migration of tumor from the original tumor site to other tissues or organs);
Track the distribution of cells in the body, These can in turn enable researchers to;
Detect solid tumors;
Give a personalized treatment depending on the individual's physiological condition, as opposed to a general prescribed treatment; and
Monitor the effectiveness of the therapeutic treatment.

We may combine the above embodiments and specifications to generate new embodiments. It will be apparent that improvements and modifications may be made within the purview of the invention without departing from the scope of the inventions.

REFERENCES

A. Apollo, B. Holt, K. Lai, H. Mak, A. Mendelson, 2006, Heating of Nanoshells by Near-infrared Radiation: A rapid and Minimally-invasive method for destroying tumors, http://ecommons.library.cornell.edu/bitstream/1813/3062/1/group12.pdf.

B. P. Martins, 2006, New Topics in Superconductivity Research, Google Book, http://books,google.com/books?id=jbkOU216MDoC&pg=PA125&lpg=PA125&dq=% 22levitation+gap%22+mm+superconductor&source=web&ots=j8VntOUaCA&sig=D4FVULRLFGhYr6991dM Xd19bxEM&hl=en&sa=X&oi=book_result&resnum=9&ct=result#PPP1,M1

D. P. O'Neal., L. R. Hirsch, N. J. Halas, J. D. Payne, J. L. West, 2004, Photothermal tumor ablation in mice using near infrared-absorbing nanoparticles, Cancer Letters 209, 171-176.

G. D'Ovidio, F. Crisi, A. Navarra & G. Lanzara, 2006, Design and experiment of 'U' shaped iron-magnetic guideway interacting with HTS 'runner' for lift and guidance of vehicle, hnp://www.maglev2006.de/001_D'Ovidio_ok/001_D'Ovidio_ok.pdf H. M. Al-Khateeb, M. K. Alqadi, N. Y, Ayoub. 2008, Levitation Force Between a Small Magnet and Superconducting Sphere, J Supercond Nov Magn, 21: 93-96.

L. P. Hirsch, R. J. Stafford, J. A. Bankson, S. R, Sershen, B. Rivera. B. R, E, Price, J. D. Halzel, N. J. Halas, and J. West, 2003, Nanoshell-mediated near-infrared thermal therapy of tumors under magnetic resonance guidance. Proc, Natl. Acad. Sci. USA 100 (23).

X., I. Huang, H, El-Sayed, W. Qian, and M. A. El-Say, 2006, Cancer cell imaging and photothermal therapy in the near-infrared region by using gold nanorods. J. Am. Chem. Soc. 128, 2115-2120.

I. G. Chen, J. C. G. Jamn, C. C. Kuo, H. J. Liu, and M. K. Wu, Magnetic Levitation Force of Single Grained YBCO Materials, 1998, CHINESE JOURNAL OF PHYSICS VOL 36, NO. 2-11.

L. Liu, Y. Hou, C. Y. He, Z. X. Gao, L. Xiao, H. T. Ren, Y. L. Jiao, M. H. Zheng, 2008, Effect of magnetization process on levitation force between a superconducting disk and a permanent magnet, http://dean.pku.edu.cn/bksky/2000tzlwj/5.pdf.

M. K. Alqadi, H. M. Al-khateeb, F. Y. Alzoubi, N. Y. Ayoub, 2007, Effect of magnet size and geometry on magnetic levitation three. Chin. Phys. Lett. Vol. 24, No. 9, 2664.

N. D. Valle, A. Sanchez, E. Pardo, D. X. Chen, C. Navau, 2007, Optimizing levitation force and stability in superconducting levitation with translational symmetry. APPLIED PHYSICS LETTERS 90, 042503.

P. Nikitin, M. Tonto, H. Chen, and A. Rosengart, 2008, Quantitative real-time in vivo detection of magnetic nanoparticles by their nonlinear magnetization, J. Appl. Phys. 103, 07A304; DOI:10.1063/1.2830947.

S. I. Takeda, F. Mishima, and S. Nishijima, 2006, Development of magnetic force-assisted gene transfer system using biopolymer-coated ferromagnetic nanoparticles. Science and Technology of Advanced Materials, Volume 7, Issue 4, Pages 308-314.

S. Nishijima, 2008, Application of superconductivity for magnetic force control in medical and industrial fields, j.physc. 05.223.

W. M. Yang, L. Zhou, Y. Feng, P. X. Zhang, C. P. Zhang, Z. M. Yu, X. D. Tang, 2002, The effect of grain-domain-size on levitation force of melt growth processing YBCO bulk superconductors. Braz. J. Phys., vol. 32, no. 32008-10-10], pp. 763-767.

The invention claimed is:

1. A method for magnetic targeting comprising:
administering to a patient nano to micro particles that bear or are made of materials that are strongly diamagnetic so that said particles can be pushed around in a desired area inside said patient;
creating an magnetic force with a magnetic source situated externally of said particles; and
using the magnetic force to repel the particles for the purpose of moving them toward a target or for confining them in a desired target.

2. A method according to claim 1 wherein said magnetic force being applied externally from different directions in a three dimensional and controlled manners, to push said particles.

3. A method according to claim 1 further comprising using said magnetic repulsion to push, concentrate, or maintain the particles as a locus, and, if necessary, cause the locus to move.

4. A method according to claim 1 further comprising using said magnetic repulsion to shape the locus to a shape useful for a medical application.

5. A method according to claim 1 further comprising using an external energy to heat the locus to a specific temperature for medical treatment of a defined region.

6. A method according to claim 1 further comprising a targeting step for heating small area(s) of the locus with targeted external energy, such as targeted laser beam(s).

7. A method according to claim 1 further comprising using a software program to maneuver said targeting step, possibly based on information from a medical imaging system.

8. A method according to claim 1, wherein the particles inside the patient are guided to and confined to a desired location inside the patient.

9. A method according to claim 1, wherein the particles carry and/or deliver a therapeutic agent or a plurality of therapeutic agents to the desired location inside the patient.

10. A method according to claim 1; further comprising a step that creates or maintains a magnetic-gradient-focus which the magnetic gradient is nearly zero.

11. A method of magnetic targeting according to claim 1 further comprising:

administering to a patient nano to micro particles that bear or are made of materials that are strongly diamagnetic so that said particles can be pushed around in a desired area inside said patient;

creating magnetic forces with a plural of magnetic sources situated in different locations surrounding the particles; and using the external magnetic forces to repel the particles so to move them toward a desired location or to confine them in desired relative locations.

12. A method according to claim 11, wherein the particles inside the patient are guided to and confined to a desired location inside the patient.

13. A method according to claim 11, wherein the particles carry and/or deliver a therapeutic agent or a plurality of therapeutic agents to the desired location inside the patient.

14. A method according to claim 11 wherein said magnetic forces come from either opposite or near opposite directions or stereo from three or more directions.

15. A method according to claim 11 further comprising a step that creates or maintains a magnetic-gradient-focus which the magnetic gradient is nearly zero.

* * * * *